(12) United States Patent
Besz et al.

(10) Patent No.: US 8,606,347 B2
(45) Date of Patent: Dec. 10, 2013

(54) CATHETER LOCATOR APPARATUS AND METHOD OF USE

(75) Inventors: William John Besz, Parkside (AU); Donald Philip Chorley, Parkside (AU); Stuart Brasted, Parkside (AU); Robert Anthony Walker, Hawthorndene (AU); Kathleen Maria Walker, legal representative, Hawthorndene (AU)

(73) Assignee: Corpak MedSystems, Inc., Buffalo Grove, IL (US)

( * ) Notice: Subject to any disclaimer, the term of this patent is extended or adjusted under 35 U.S.C. 154(b) by 0 days.

(21) Appl. No.: 13/570,999

(22) Filed: Aug. 9, 2012

(65) Prior Publication Data

US 2013/0035589 A1   Feb. 7, 2013

Related U.S. Application Data

(63) Continuation of application No. 12/646,263, filed on Dec. 23, 2009, now Pat. No. 8,265,732, which is a continuation of application No. 10/362,273, filed as application No. PCT/AU01/01051 on Aug. 23, 2001, now abandoned.

(30) Foreign Application Priority Data

Aug. 23, 2000 (AU) .................................. PQ 9592
May 24, 2001 (AU) .................................. PR 5250

(51) Int. Cl.
    *A61B 5/05*     (2006.01)
(52) U.S. Cl.
    USPC ......................................... 600/424; 600/407

(58) Field of Classification Search
    USPC ................................................... 600/407, 424
    See application file for complete search history.

(56) References Cited

U.S. PATENT DOCUMENTS

| | | | |
|---|---|---|---|
| 4,173,228 A | 11/1979 | Van Steenwyk et al. |
| 4,317,078 A | 2/1982 | Weed et al. |
| 4,572,198 A | 2/1986 | Codrington |
| 4,672,972 A | 6/1987 | Berke |
| 4,905,698 A | 3/1990 | Strohl, Jr. et al. |
| 5,005,592 A | 4/1991 | Cartmell |
| 5,042,486 A | 8/1991 | Pfeiler et al. |
| 5,045,071 A | 9/1991 | McCormick et al. |
| 5,099,845 A | 3/1992 | Besz et al. |

(Continued)

FOREIGN PATENT DOCUMENTS

| | | |
|---|---|---|
| AU | 1989PJ4337 | 5/1989 |
| AU | 642647 | 10/1993 |

(Continued)

OTHER PUBLICATIONS

1P Series Catalogue.

(Continued)

*Primary Examiner* — James Kish
(74) *Attorney, Agent, or Firm* — K&L Gates LLP

(57) ABSTRACT

In one embodiment, a catheter locator apparatus is configured to determine the location of the tip of a catheter as it is inserted used in a human body. In one example embodiment, where a radiating coil is used in conjunction with a catheter, a coil locating device can be used to determine the distance the coil is from the device and hence its depth in the body of a patient.

28 Claims, 8 Drawing Sheets

(56) References Cited

U.S. PATENT DOCUMENTS

| | | |
|---|---|---|
| 5,211,165 A | 5/1993 | Dumoulin et al. |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,265,610 A | 11/1993 | Darrow et al. |
| 5,273,025 A | 12/1993 | Sakiyama et al. |
| 5,279,607 A | 1/1994 | Schentag et al. |
| 5,325,873 A | 7/1994 | Hirschi et al. |
| 5,353,795 A | 10/1994 | Souza et al. |
| 5,353,807 A | 10/1994 | DeMarco |
| 5,375,596 A | 12/1994 | Twiss et al. |
| 5,377,678 A | 1/1995 | Dumoulin et al. |
| 5,386,828 A | 2/1995 | Owens et al. |
| 5,391,199 A | 2/1995 | Ben-Haim |
| 5,395,366 A | 3/1995 | D'Andrea et al. |
| 5,425,367 A | 6/1995 | Shapiro et al. |
| 5,429,132 A | 7/1995 | Guy et al. |
| 5,437,277 A | 8/1995 | Dumoulin et al. |
| 5,443,066 A | 8/1995 | Dumoulin et al. |
| 5,443,489 A | 8/1995 | Ben-Haim |
| 5,445,150 A | 8/1995 | Dumoulin et al. |
| 5,480,422 A | 1/1996 | Ben-Haim |
| 5,546,951 A | 8/1996 | Ben-Haim |
| 5,558,091 A | 9/1996 | Acker et al. |
| 5,584,838 A | 12/1996 | Rona et al. |
| 5,592,939 A | 1/1997 | Martinelli |
| 5,622,169 A | 4/1997 | Golden et al. |
| 5,645,065 A | 7/1997 | Shapiro et al. |
| 5,669,383 A | 9/1997 | Johnson |
| 5,681,260 A * | 10/1997 | Ueda et al. ............ 600/114 |
| 5,699,801 A | 12/1997 | Atalar et al. |
| 5,711,299 A | 1/1998 | Manwaring et al. |
| 5,713,946 A | 2/1998 | Ben-Haim |
| 5,718,241 A | 2/1998 | Ben-Haim et al. |
| 5,727,553 A | 3/1998 | Saad |
| 5,729,129 A | 3/1998 | Acker |
| 5,730,129 A | 3/1998 | Darrow et al. |
| 5,738,096 A | 4/1998 | Ben-Haim |
| 5,752,513 A | 5/1998 | Acker et al. |
| 5,762,064 A | 6/1998 | Polvani |
| 5,769,843 A | 6/1998 | Abela et al. |
| 5,792,055 A | 8/1998 | McKinnon |
| 5,795,298 A | 8/1998 | Vesely et al. |
| 5,797,849 A | 8/1998 | Vesely et al. |
| 5,810,728 A | 9/1998 | Kuhn |
| 5,817,022 A | 10/1998 | Vesely |
| 5,827,202 A | 10/1998 | Miraki et al. |
| 5,830,144 A | 11/1998 | Vesely |
| 5,833,608 A | 11/1998 | Acker |
| 5,840,024 A | 11/1998 | Taniguchi et al. |
| 5,840,025 A | 11/1998 | Ben-Haim |
| 5,843,002 A | 12/1998 | Pecor et al. |
| 5,846,198 A | 12/1998 | Killmann |
| 5,868,673 A | 2/1999 | Vesely |
| 5,868,674 A | 2/1999 | Glowinski et al. |
| 5,879,297 A | 3/1999 | Haynor et al. |
| 5,882,304 A | 3/1999 | Ehnholm et al. |
| 5,899,860 A | 5/1999 | Pfeiffer et al. |
| 5,902,238 A | 5/1999 | Golden et al. |
| 5,906,579 A | 5/1999 | Vander Salm et al. |
| 5,913,820 A | 6/1999 | Bladen et al. |
| 5,916,162 A | 6/1999 | Snelten et al. |
| 5,936,406 A | 8/1999 | Potthast |
| 5,938,603 A | 8/1999 | Ponzi |
| 5,941,858 A | 8/1999 | Johnson |
| 5,944,023 A | 8/1999 | Johnson et al. |
| 5,951,472 A | 9/1999 | Van Vaals et al. |
| 5,954,665 A | 9/1999 | Ben-Haim |
| 5,964,757 A | 10/1999 | Ponzi |
| 6,016,439 A | 1/2000 | Acker |
| 6,019,725 A | 2/2000 | Vesely et al. |
| 6,024,739 A | 2/2000 | Ponzi et al. |
| 6,047,214 A | 4/2000 | Mueller et al. |
| 6,059,718 A | 5/2000 | Taniguchi et al. |
| 6,064,905 A | 5/2000 | Webster et al. |
| 6,066,094 A | 5/2000 | Ben-Haim |
| 6,073,043 A | 6/2000 | Schneider et al. |
| 6,076,007 A | 6/2000 | England et al. |
| 6,087,831 A | 7/2000 | Bornert et al. |
| 6,104,944 A | 8/2000 | Martinelli |
| 6,129,668 A | 10/2000 | Haynor et al. |
| 6,161,032 A | 12/2000 | Acker |
| 6,173,199 B1 | 1/2001 | Gabriel |
| 6,185,448 B1 | 2/2001 | Borovsky |
| 6,201,387 B1 | 3/2001 | Govari |
| 6,201,987 B1 | 3/2001 | Dumoulin |
| 6,203,493 B1 | 3/2001 | Ben-Haim |
| 6,211,666 B1 | 4/2001 | Acker |
| 6,216,026 B1 | 4/2001 | Kuhn et al. |
| 6,216,027 B1 | 4/2001 | Willis et al. |
| 6,216,028 B1 | 4/2001 | Haynor et al. |
| 6,223,066 B1 | 4/2001 | Govari |
| 6,226,547 B1 | 5/2001 | Lockhart et al. |
| 6,230,038 B1 | 5/2001 | Von Gutfeld et al. |
| 6,230,042 B1 | 5/2001 | Slettenmark |
| 6,233,476 B1 | 5/2001 | Strommer et al. |
| 6,235,038 B1 | 5/2001 | Hunter et al. |
| 6,236,879 B1 | 5/2001 | Konings |
| 6,246,231 B1 | 6/2001 | Ashe |
| 6,263,230 B1 | 7/2001 | Haynor et al. |
| 6,272,370 B1 | 8/2001 | Gillies et al. |
| 6,298,257 B1 | 10/2001 | Hall et al. |
| 6,298,261 B1 | 10/2001 | Rex |
| 6,304,769 B1 | 10/2001 | Arenson et al. |
| 6,332,089 B1 | 12/2001 | Acker et al. |
| 6,366,799 B1 | 4/2002 | Acker et al. |
| 6,374,134 B1 | 4/2002 | Bladen et al. |
| 6,427,079 B1 | 7/2002 | Schneider et al. |
| 6,432,041 B1 * | 8/2002 | Taniguchi et al. ............ 600/118 |
| 6,445,943 B1 | 9/2002 | Ferre et al. |
| 6,473,635 B1 | 10/2002 | Rasche |
| 2001/0045826 A1 | 11/2001 | Schneider |
| 2002/0161306 A1 | 10/2002 | Govari |
| 2002/0161421 A1 | 10/2002 | Lee et al. |

FOREIGN PATENT DOCUMENTS

| | | |
|---|---|---|
| AU | 2000PQ9592 | 8/2000 |
| AU | 2001PR5250 | 5/2001 |
| CA | 1330108 | 6/1994 |
| CA | 2218093 | 10/1996 |
| CN | 1049288 | 2/1991 |
| DE | 19830183 A1 | 7/1999 |
| EP | 359697 B1 | 3/1990 |
| EP | 399536 | 5/1991 |
| EP | 846959 A1 | 6/1998 |
| WO | 90/02514 A1 | 3/1990 |
| WO | 93/04628 | 3/1993 |
| WO | 96/05768 A1 | 2/1996 |
| WO | 96/07352 | 3/1996 |
| WO | 96/32060 A1 | 10/1996 |
| WO | 97/29683 A1 | 8/1997 |
| WO | 02/15973 A1 | 2/2002 |

OTHER PUBLICATIONS

A Novel Technique for Nasoduodenal Feeding Tube Placement in Critically Ill Patients, dated Feb. 14, 2002.

Biosense Webster, A Johnson & Johnson Company, CARTO™ EP Navigation System, printed from http://www.biosensewebster.com/US/products_cartonav.htm, Oct. 23, 2002.

Biosense Webster, A Johnson & Johnson Company, CUSOMCATH™ Program, printed from http://www.biosensewebster.com/US/products.htm, Oct. 23, 2002.

Cathlocator™ from www.micronix.com printed on Oct. 25, 2002.

Department of Health and Human Services, Navi-Star Diagnostic/Ablation Deflectable Tip Catheter, Food and Drug Administration, Jun. 15, 2000.

EVIS 140 Series, Olympus, printed from http://www.olympus.co.jp, Oct. 22, 2002.

EVIS 240 Series, Olympus, printed from http://www.olympus.co.jp, Oct. 22, 2002.

(56) References Cited

OTHER PUBLICATIONS

Extender cable graphic, manufactured by LEMO USA Inc., distributed and sold by HLC Ltd as of Jul. 29, 2002.
Flow Through Stylet Connector, Corpak MedSystems, Aug. 19, 1987.
FMN Connector, Connectors for FFC, written by JST, pp. 390-391.
GIF-N30 Fiberscope, Olympus® Focus on Life, printed from http://www.olympusamerica.com/msg_section, Oct. 22, 2002.
GIF-XP160, Olympus® Focus on Life, printed from http://www.olympusamerica.com/msg_section, Oct. 22, 2002.
LEMO's Push-Pull Self-Latching Connection System, p. 5, LEMO USA Inc.
Lucent® Medical Systems, Adding Intelligence to Indwelling Devices, printed from http://www.lucentmedical.com/overview2.htm, Oct. 23, 2002.
Lucent® Medical Systems, Enteral Feeding Tubes, printed from http://www.lucentmedical.com/et.htm, Oct. 23, 2002.
Lucent® Medical Systems, The LMS-ZortanTM, printed from http://www.lucentmedical.com/zortan.htm, Oct. 23, 2002.
Luminal Devices, The Cathlocator: A novel non-radiological method for the localization of enteral tubes, Journal of Gastroenterology and Hepatology (1996) 11, pp. 500-505.
Multiple Leision™ FFR of Serial Tandem Lesions, Florence Medical, printed from http://www.florencemedical.com, Oct. 22, 2002.
NAVI-STAR® Diagnostic/Ablation Deflectable Tip Catheter, U.S. Food and Drug Administration—Center for Devices and Radiological Health, printed in Oct. 2002.
News from NAVION™ printed from http://www.navionbiomedical.com/system.htm, Oct. 23, 2002.
Olympus Medical Endoscope & Surgical Products, Olympus, printed from http://www.olympus.co.jp/en/mesg/endoscope, Oct. 22, 2002.
Olympus Medical Endoscope & Surgical Products, Olympus, printed from http://www.olympus.co.jp/LineUp/Endoscope/indexE.html, Oct. 17, 2002.
Olympus® Focus on Life, CF-Q160AL, printed from http://www.olympusamerica.com/msg_section, Oct. 22, 2002.
Olympus® Focus on Life, CF-Q160S, printed from http://www.olympusamerica.com/msg_section, Oct. 22, 2002.
Radio-Frequency Interface—An EMC Study of the Cathlocator™, Institute of Technology, Department of Biomedical Engineering, Master's Thesis, Dec. 20, 2002.
Research in Catheter and Tube Placement, Navion Biomedical, printed from http://www.navionbiomedical.com/system.htm, Oct. 23, 2002.
Selection of contact types, p. 9, LEMO USA Inc.
SmartFlow® Family of Product Simultaneous CFR/FFRTM, Floerence Medical, printed from http://www.florencemedical.com/system.htm, Oct. 23, 2002.
The NAVION™ BioNavigation System, Navion Biomedical, printed from http://www.navionbiomedical.com/system.htm, Oct. 23, 2002.
European Search Report mailed Nov. 3, 2010 for corresponding European Appln. No. 10008275.9.

* cited by examiner

CATHETER LOCATOR APPARATUS AND METHOD OF USE

CROSS REFERENCE TO RELATED APPLICATIONS

The present application is a continuation that claims priority to and the benefit of U.S. patent application Ser. No. 12/646,263, filed Dec. 23, 2009, now U.S. Pat. No. 8,265,732 which is a continuation that claims priority to and the benefit of U.S. patent application Ser. No. 10/362,273, filed on Feb. 21, 2003, now abandoned which is a 35 U.S.C. §371 filing based on PCT/AU01/01051 filed on Aug. 23, 2001, which claims priority and the benefit of Australian Patent Application No. PR 5250 filed in the Australian Patent Office on May 24, 2001, and Australian Patent Application No. PQ 9592 filed in the Australian Patent Office on Aug. 23, 2000, the entire contents of each of which are incorporated herein by reference.

This invention relates to a method of catheter and radiating coil location in a human body and in particular to the determination over time of the location of the tip of a catheter as it is inserted and during its use in the body and/or its route through the body.

BACKGROUND

For ease of explanation, the guidance and placement and ongoing maintenance of a catheter for enteral nutrition will be described in one example in this specification. It will however be clear to the person skilled in the art that the techniques and equipment described are useful for similar placement requirements in other parts of the human body and animal bodies as well. Catheters are used for many different purposes and there exist many different catheter types. An example of the use of the invention in a human body will also be provided in the field of Central Venous Catheter location.

Enteral nutrition includes both the ingestion of food orally and the non-volitional delivery of nutrients by tube into the gastrointestinal tract. Patients are candidates for enteral tube feeding that will not, should not, or cannot eat but who have a functional gastrointestinal tract. Benefits of enteral tube feeding are the maintenance of gastrointestinal structure and functional integrity, enhanced utilization of nutrients, ease and safety of administration.

Enteral tube feeding is contraindicated for patients with diffuse peritonitis, intestinal obstruction that prohibits use of the bowel, intractable vomiting, paralytic ileus, and/or severe diarrhoea that makes metabolic management typical. Other potential contraindications that depend on the clinical circumstances include severe pancreatitis, enterocutaneous fistulae, and gastrointestinal ischemia. Enteral tube feeding is not recommended during the early stages of short-bowel syndrome or in the presence of severe malabsorption.

The route selected for tube feeding depends upon the anticipated duration of feeding, the condition of the gastrointestinal tract (e.g. esophageal obstruction, prior gastric or small-bowel resections), and the potential for aspiration. The intestine can be accessed at the bedside (naso intestinal tube, naso endoscopic gastrostomy) or in the operating room (gastrostomy and jejunostomy).

Nasal intubation for gastric feeding is the simplest and most often used method for tube feeding. This technique is preferred for patients who are expected to eventually resume oral feeding. Maximal patient comfort and acceptance is more likely when a soft feeding tube with a small external diameter is used. Access to the duodenum and jejunum is possible with longer tubes but placement of the tip into the duodenum and jejunum is more difficult and time consuming and has added risk factors.

Enteral tube feeding is considered safer than parenteral nourishment because mechanical, infection, and metabolic complications are usually less severe than those encountered with parenteral nutrition. However, enteral feeding is not problem free, and significant complications can occur when the tube and feeding is managed by unskilled or untrained individuals or if monitoring is absent or inappropriate.

Incorrect placement of the feeding tube is one of a number of major complications. Most serious is the unintended placement of the catheter during nasal intubation into the cardiovascular system or into the lungs. Both of these situations are possible when inexperienced medical staff perform intubation. A stylet (relatively stiff small gauge wire) is used to stiffen and support the otherwise flaccid catheter tube during its intubation.

It is also prudent to check that the exit aperture of the feeding tube (typically located at the distal end/tip of the tube) remains in its desired location over the period of feeding. Protocols that address this requirement include frequent monitoring for the appropriate pH of fluids extracted from the feeding tube while not carrying nutritional liquids and careful patient monitoring to ensure that nutritional uptake is as expected.

X-rays are often used to determine the location of the caudal/distal end of the tube. However, even X-rays are not necessarily conclusive as to its location. The natural and continuous movement of the internal organs can make it difficult for the physician interpreting the X-ray to be sure of the actual location of the caudal/distal end of the tube because the movement described can change the position of the catheter over time.

There exist a large variety of catheters, their names sometimes indicating their use, the part of the body they enter or treat and sometimes they are named after the physician or physicians who developed methodologies for their use.

This invention also relates to catheter location methods and means for central venous catheters.

Intravenous catheters are those that access the interior of a patient via an opening in the skin passed down one or more of the many branches of the venous system to the region requiring medical attention. These types of catheters are also referred to as Venous Access Catheters (VAC) and Central Venous Catheters (CVCs) and are used generally in the cardiovascular system.

A sub-category of intravenous catheters is those that fall under the heading of Peripherally Inserted Central Catheter (PICC). These catheters have been used by clinicians for many years and many different techniques exist for their insertion.

One such insertion technique is the Seldinger technique and along with advances in devices and materials there now exists a modified Seldinger technique, useful particularly for small or poor veins.

There exist a large selection of intravenous catheters such as for example peripheral catheters which are used for insertion into the body that are from one half to three inches in length; midline catheters which are used for insertion being greater than three inches in length; mid-clavicular and non-tunneled sub-clavian, tunneled Groshong, Hickman and Broviac or subcutaneous implanted ports for longer lengths.

Common to intravenous catheters is the use of a guide wire that is passed into the body and into a vein and then directed by the skill of the clinician to the desired location. Once the guide wire is in place a catheter is slid over its external free end and pushed till the distal end of the catheter reaches the end of the guide wire.

The location of the tip of these types of catheters or the recordal of the advancement of the guide wire into the body is achieved in a number of ways.

Return checks are used to expire types of liquids expected to be at or near the tip of the catheter and the checking of length markings on the wires used within catheters are two methods used by clinicians who do not have ready access to alternatives. Ultrasound guidance, fluoroscopy and X-ray methodologies are preferred even though they do not always provide an exact determination of the location of the tip or path of the guide wire or catheter.

More expensive and more lime-consuming CT examinations provide the best means of locating not only the tip but also the path of any of the types of catheter described above and others that are located in the body of a patient.

The final location of the caudal/distal end of any catheter is critical to the efficacy of the purpose for the use of the catheter. In one example, the delivery of drugs directly into the heart can be best achieved by the location of the caudal/distal end of the catheter in the superior vena cava (CVC). Studies show that it is preferable to locate the caudal/distal end of the catheter in the upper portion of the superior vena cava (typically recognised as being more than 4.5 cm above the cavoatrial junction). Studies indicate that these preferable locations appear to minimise catheter malfunction.

More critical however, is to ensure that the catheter is in the superior vena cava itself, as there exist studies indicating that there is a significant association between catheter malfunction and catheter tip location in the venous system adjacent to the superior vena cava.

FIG. 7 depicts the various veins in the vicinity of and including the superior vena cava.

Where for example, the catheter tip is in either of the brachiocephilac veins or near the junction of a brachiocephilac vein there is a greater likelihood of the unwanted development of a fibrin sheath or the presence of thrombus around or at the tip of the catheter as compared to catheter tips located in the superior vena cava. Greater likelihood of unwanted developments can occur when a catheter tip is located in the sub-clavian vein or the cavoatrial junction or in the right atrium.

The effect of inappropriate or less than ideal catheter tip location is shortened survival which clearly is manageable but more serious effects may include thrombosis and phlebitis infections more, particularly pheumothorax infections and, in more serious situations, occlusions.

When catheter tips suffer thrombosis, these studies demonstrate significantly shorter survival than those catheters that are not subject to this unwanted development.

Appropriate patient care requires consideration of a large number of factors when considering the need for intravenous catheter usage. Sometimes the benefit of drug delivery has to be carefully weighed against the likelihood of adverse effects of intravascular device related infections as mentioned previously.

Catheter selection is not a simple matter and factors to be considered include the following:
    type of medication
    osmolarity and pH of the solution to be infused
    duration of therapy required
    secondary risk factors and chronic diseases
    patient age, activities, work and lifestyle
    future intravenous needs and long term prognosis
    current availability and status of access veins (typically peripheral veins of the limbs)
    patient history of neurologic impairments, surgeries affecting veins or lymphatic system, bloods dyscrasias, thrombosis and previous intravenous use history
    current patient diagnosis and preferences for treatment The anticipated duration of therapy can readily suggest short peripheral catheters for periods of less than five days, and for periods of less than four weeks a midline catheter is generally suitable.

Middavicular lines are an option and becoming more popular as the occurrence of thrombosis resulting from sub-optimal placement in sub-clavian regions other than the superior vena cava increase.

In fact mid-clavicular lines are often used in home care situations to avoid the time and cost of confirmatory X-rays. However, even mid-clavicular lines need to be optimally placed in the lower one third of the superior vena cava, dose to the junction of the superior vena cava and the right atrium but should not advance into the right atrium itself.

The previously mentioned Peripherally Inserted Central Catheters (PICCs) having a tip location in the superior vena cava can be used for long term therapy (five days to one year). However, they should be critically checked by X-ray to determine appropriate tip placement even though this is neither a totally satisfactory nor certain method of location checking.

It is thus a real need for physicians to be able to increase their confidence that the catheter has been placed at the desired location and remain there in the body of their patient. This is so whether that is for the purpose of enteral and parenteral nutrition, receiving vesicant chemotherapeutic agents, antibiotics and blood sampling or for other purposes.

BRIEF DESCRIPTION OF ME INVENTION

A broad form of the invention is a method of locating a coil used in relation to a catheter to be inserted into a subject body wherein said coil radiates signal energy; the method including the steps of: using a coil position measuring means having at least two signal energy detectors wherein said measuring means is located with reference to a predetermined location on or part of said subject human body; and displaying a position measurement made by said coil position measuring means wherein said position measurement is relative to said position measuring means for use by a clinician in determining the position of said coil and said catheter in said subject human body relative to said predetermined location on or part of said subject human body.

In a further aspect of the invention, the method includes the further step of also displaying with said position measurement a representation of a point or region of a non-subject body referenced to said displayed position measurement for use by the clinician in determining the position of said coil and said catheter in said subject human body.

3. In another aspect of the invention, the position measuring means is located with reference to a predetermined location being on or over the xiphoid sternal junction of said human body for use with a catheter inserted into the alimentary canal.

In another aspect of the invention, a region or delineation of a body part is displayed that is representative of the diaphragm of a non-subject human body thus delineating on said display the upper and lower chest cavities of a human body.

In another aspect of the invention, the position measuring means is located with reference to a predetermined location being on or over the caudal/mid sagital aspect of the jugular sternal notch of said human body use with a catheter inserted into the cardiovascular or respiratory system.

In yet a further aspect of the invention, a region or delineation of a body part is displayed that is representative of the sternum of the said human body thus delineating on said display a portion of the upper skeleton of a human body.

In a yet further aspect of the invention, the method includes the further step of displaying a position measurement of said coil at predetermined intervals of time.

In a further aspect of the invention, the coil is incorporated into a stylet or guide wire adapted for use with a catheter.

In yet a further aspect of the invention, the method includes the further step of displaying the position of said coil at predetermined intervals of time while said stylet or guide wire is retracted from a catheter so that the path of said coil and thus said catheter can be tracked and displayed.

In an aspect of the invention, a coil is incorporated into a catheter and usable for locating the position of said catheter in a human body.

In another aspect of the invention a catheter locator apparatus for assisting a user's placement of a catheter into a subject body comprises: a pair of wires usable with the catheter, the wires having a first end and a second end; a processor in electronic communication with the first end of the wires; a radiating coil connected to the second end of the wires, the radiating coil having various locations in the subject body; a detector device in electronic communication with the processor, the detector device adapted to be positioned in relation to a predetermined portion of the subject body; reference data retrieved by the processor which specifies at least one reference image which represents at least one predetermined image; indicator data generated by the processor which specifies at least one indicator image which provides information related to at least one location of the radiating coil in the subject body; and a monitor in electronic communication with the processor which displays the indicator image and the reference image.

In yet a further aspect of the invention a catheter adapted for use with a catheter locator apparatus includes: (a) a processor in electronic communication with a coil; (b) the coil radiating and incorporated into a coil positioning device, stylet, guide wire or into said catheter, the radiating coil having various locations in a subject body; (c) a detector device in electronic communication with the processor; (d) reference data generated by the processor which specifies at least one reference image which represents at least one predetermined portion of the subject body; (e) indicator data generated by the processor which specifies at least one indicator image which provides information related to at least one location of the radiating coil in the subject body; and (f) a monitor in electronic communication with the processor which displays the indicator image and the reference image, said catheter comprising: a tube which is adapted to receive the stylet or guide wire or having a coil incorporated thereto, the tube having a proximal end and a distal end; and a tip included at the distal end.

A yet further aspect of the invention is a catheter locator apparatus comprising: a multi stranded wire insertable into a catheter, the wire having a proximal end and a distal end; a radiating coil connected to the distal end of two of the strands in said wire; at least two receiving coils; a monitor; a processor, in electronic communication with the wire, the receiving coils and the monitor, which: the processor receives at least one reference signal from at least two of the receiving coils after the receiving coil is positioned with reference to at least one predetermined bony landmark on the subject body; and retrieves reference data; and drives the monitor in order to graphically represent the reference data; and receives at least one indicator signal from the at least two receiving coils that receive a signal from the radiating coil after the radiating coil is inserted into the subject body; as well as generates indicator data; and drives the monitor in order to graphically represent the indicator data.

Another method of facilitating proper placement of a catheter into a subject body, the method comprises the steps of:
(a) receiving at least one reference signal indicative of a location of at least one receiving coil positioned with reference to a predetermined landmark on the subject body;
(b) receiving at least one indicator signal from a radiating coil inserted into the subject body;
(c) retrieving reference data associated with the predetermined landmark;
(d) displaying a reference image derived from the reference data;
(e) generating data represented by an indicator signal indicative of the relative position of the at least two receiving coil positions on or over the subject body;
(f) displaying graphics represented by the indicator data; and
(g) repeating steps (e) and (f) after a change in the indicator signal is received.

A further method of operating a catheter locator apparatus, comprises the steps of:
(a) placing a predetermined area of a detector device over a predetermined landmark on a subject body;
(b) inserting a catheter, stylet, guide wire or coil locating device, embedded with a radiating coil, into the subject body;
(c) viewing a graphical representation of a predetermined part or portion or a representation of a reference image on a monitor;
(d) viewing a graphical representation of the radiating coil on a monitor; and
(e) manipulating the catheter in the subject body with aid of the display of the relative positions of the graphical representations.

A yet further aspect of the invention comprises a wire bundle for use with a catheter locator apparatus that includes:
(a) a processor in electronic communication with a predetermined portion of a proximal end of the wire bundle; (b) a radiating coil connected to a predetermined portion of a distal end of the wire bundle, the radiating coil having various locations in a subject body; (c) a detector device in electronic communication with the processor, the detector device adapted to be positioned in relation to a predetermined portion of the subject body; (d) reference data retrieved by the processor which specifies at least one reference image which represents at least one predetermined image; (e) indicator data generated by the processor which specifies at least one indicator image which provides information related to at least one location of the radiating coil in the subject body; and (f) a monitor in electronic communication with the processor which displays the indicator image and the reference image, said wire bundle comprising:
    a first wire having a predetermined stiffness adapted to control positioning of a flexible tube;
    a second wire adapted to transmit signals between the radiating coil and the processor; and
    means for binding the second wire to the first wire.

Specific embodiments of the invention will now be described in some further detail with reference to and as illustrated in the accompanying figures. These embodiments are illustrative, and are not meant to be restrictive of the scope of the invention.

Suggestions and descriptions of other embodiments may be included within the description of the invention but may not be illustrated in the accompanying figures or alternatively features of the invention may be shown in the figures but not described in the specification.

DETAILED DESCRIPTION OF EMBODIMENTS OF THE INVENTION

Figure 1:
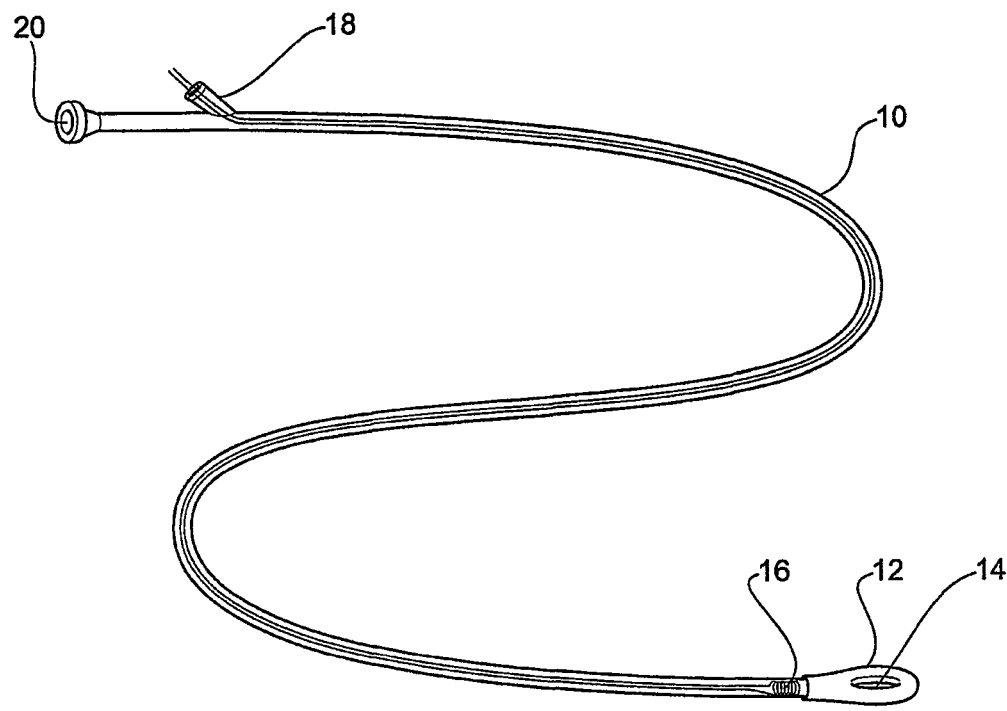
FIG. 1 depicts a catheter having a coil and exit aperture located near its caudal/distal end.

FIG. 1 depicts a single lumen catheter having located near its caudal/distal end, a coil, which is used to emit a signal that can be detected by an apparatus not unlike that described in U.S. Pat. No. 5,099,845. That patent is in the name of Micronix Pty Ltd and is hereby incorporated into this specification by reference. The incorporation of the above-mentioned patent does not and should not be construed as an admission of the content of the specification having entered the common general knowledge of those skilled in the art.

The apparatus of the invention described in the above-mentioned patent provides a means to determine both the depth and position of a coil located on the end of a catheter as well as its orientation. The type of catheter is of no great importance to the principle and method of the invention.

The depth and position determining apparatus, also referred to herein as the detector apparatus, is generally of the type disclosed in the above-mentioned specification and can be used in the method described herein but is not the only such device that will provide the required features.

The catheter 10 depicted in FIG. 1 is suitable for use in parenteral nutrition in particular as it has a suitable tip shape 12 designed so that the exit aperture 14 is less likely to become blocked. The catheter shown has a single lumen (single passageway from proximal to caudal/distal end) but other catheters may have multiple lumens.

A coil 16 is located near the tip 12 and the two ends of the pair of wires, which will run the length of the catheter. The pair of wires terminates at connector 18 near the proximal end of the catheter. The entry aperture 20 to the catheter is located at the extreme proximal end of the catheter. It is into this aperture that nutrients are pumped at the desired times and rates once the caudal/distal end of the catheter has been appropriately located within the patient.

It is intended that the connectors for catheters used for different uses will each be different sizes, connection types and colors so as to make their use as safe as possible. By making the interconnection of catheters for different applications difficult if not impossible, it is intended to minimize accidental administration of the incorrect or inappropriate fluids particularly drugs to the patent via catheters not intended for such use.

When the catheter 10 is being intubated into the gastrointestinal tract of the patient, a metal stylet is used within the catheter.

Figure 2:
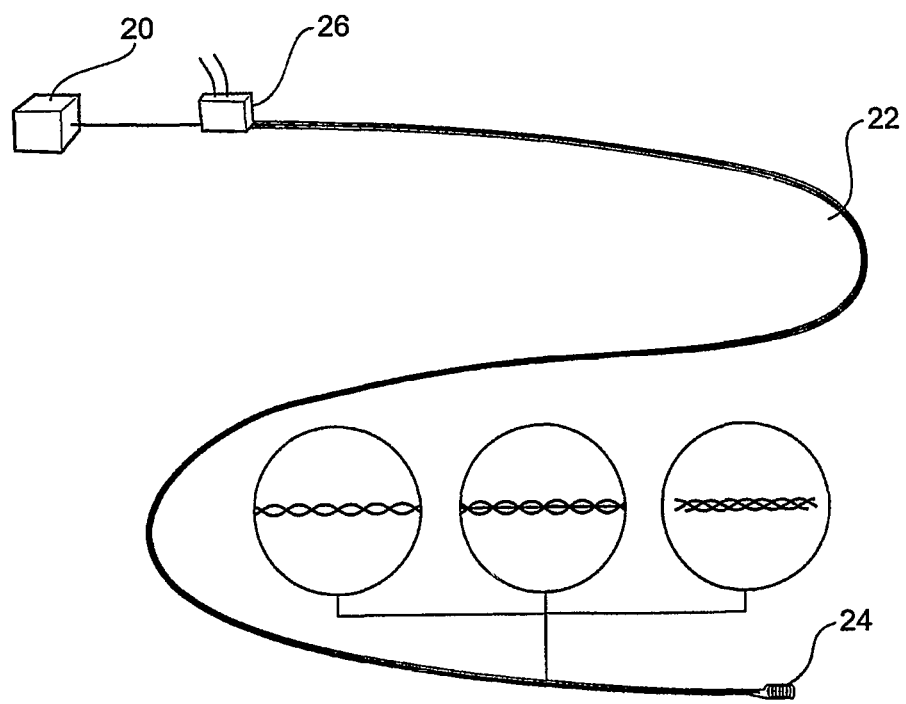
FIG. 2 depicts a stylet having a coil located near its caudal/distal end.

The stylet can comprise the pair of wires described previously or can comprise the typical stylet wire or wires having a pair of wires incorporated therein. The stylet may be encapsulated in material know to be suitable for its intended use. The stylet itself is typically made of stainless steel but it could also be made of plastic or other suitable material as shown in FIG. 2.

In one embodiment, the processor is connected to a proximal end of a wire bundle, and the coil is connected to the distal end of the wire bundle. The wire bundle includes a guide wire suitably bound to a signal-carrying wire/s. The bundle is preferably bound together at its ends and along its length and may also be encapsulated in material know to be suitable for its intended use. The bundle may for example be wrapped together or wrapped with a suitable material, it may be maintained by a suitable adhesive or fastener or suitable size and shape. See FIG. 2

Intubation can be via the mouth or preferably via a nasal passageway of the patient. The stylet stiffens the otherwise formless catheter and is able to be manipulated along its length as well as at its proximal end, so that its caudal/distal end navigates an appropriate route through the patient under the control of the health professional or trained staff performing the intubation.

In this specification, mention is made of clinicians performing intubations but it is possible for trained health professionals to insert catheters into patients for a variety of uses. It is also possible to use a suitably stiff catheter having a coil incorporated into the wall of the catheter typically at or near the caudal/distal end of the catheter that has a single lumen used to deliver the appropriate fluids.

The inventors have identified that there are economic and practical reasons why the arrangement of a coil integrated into a catheter is usable. However, it is less desirable than an alternative arrangement to be described herein which uses the stylet to carry the radiating coil.

The above is so, because the catheter/coil combination is expensive to manufacture to the high standards required of medical equipment. Catheter manufacturers provide a specialist product and it is not always in their interest to incorporate changes that will markedly increase the cost of their product.

Furthermore, a catheter/coil combination is a single use item, thus the added value of the coil is not recoverable and therefore needs to compete with current detection techniques which involve X-rays, even though they are more time consuming.

Thus it has been identified that it is possible to incorporate a coil into the caudal/distal end of a stylet.

The stylet is used not only to manipulate the caudal/distal end of the catheter to a desired location but it can be retracted and is also capable of being reused after appropriate decontamination and cleaning according to a required protocol. The inventors do not recommend such reuse unless a relevant protocol is in place.

The depth and position of the coil can be determined during the process of intubation. Furthermore, when used to locate the tip of a catheter and following appropriate positioning of the caudal/distal end of the catheter the route of the catheter can be determined while the stylet is retracted from the catheter. An example of the trace displayed after a retraction of the stylet is provided by FIG. 6 the details of which will be described later in the specification. A stylet with a coil incorporated thereon can also be used to determine the location in the patient of particular locations along the length of the catheter. Thus for multiple lumen catheters that have a plurality of ports along its length the location in the patient of each of those ports can be determined.

The manufacture of a coil on the end of a stylet is not trivial but it can be automated and will involve only a few different materials, not the many different material and processes involved in the manufacture of a catheter/coil combination as described above.

As described previously a particularly advantageous feature of a coil being incorporated into a stylet is that while the stylet and coil is being retracted from the catheter, it is possible for the location apparatus to record the route through the patient taken by the catheter. The route can be recorded, including its X-Y location and its depth with respect to the detection apparatus. Most conveniently, the route of the catheter can be displayed in a manner, which directly relates it to the anatomy of a patient. Appropriate positioning of the detection apparatus on the patient in the manner described later in this specification provides an ability to reference the position of the trace on the monitor with the position of internal parts of a patient.

Consequently, the procedure of re-checking the position of the caudal/distal end of the catheter and retracing the route of the catheter at future times can be easily conducted and the results compared with earlier records of the catheter tip position.

Furthermore, the route displayed will have characteristics that are likely to reassure a clinician that a desired route of the catheter has in fact been taken.

Over time, displays including depth information will correlate with other clinical observations as to the correctness of the placement and therefore increase the confidence of the clinician that the route and final placements are as they should be.

The route displayed will, within expected anatomical variation, confirm that the caudal/distal end of the catheter or other portions of the catheter are located in the desired area of the patient. For example, when locating enteral feeding catheters, the region desired is that which is in the vicinity of the jejunum, as is pictorially represented in FIG. 6.

It is also possible for these techniques to be used during the intubation process and thus provide immediate feedback as to the route being taken by the catheter.

The techniques described herein, which assist the placement of a catheter, are particularly applicable when tube enterostomies are necessary to provide long-term nutritional feeding or when obstruction makes nasal intubation impossible. A conventional gastrostomy or jejunostomy requires a surgical procedure and that is obviously preferably avoided.

Percutaneous endoscopic placement of gastric feeding tubes can be performed at the bedside or in the endoscopy suite without general anesthesia. Jejunal extensions may also be noted through a percutaneous placed gastric port into patients who require post-pyloric intestinal feeding. Needle catheter or Witzel jejunostomy placed at the time of the laparotomy allows early postoperative feeding because the small bowel is less affected than is the stomach and colon by postoperative ileus. Jejunal feedings minimize the risk of vomiting and aspiration compared with gastric feedings.

However, the techniques described herein are not a substitute for controlled administration and careful monitoring to check for residual gastric fluids. Clinical observation of the patient must be continued. The technique however, does lessen or eliminate the costly and time consuming use of X-ray facilities and expertise or other even more expensive and time consuming catheter location procedures.

FIG. 2 depicts a stylet 22 which has a coil 24 at its caudal/distal end and the proximal ends of the wires which form the coil are located in a connector base 26 and a manipulation block 28 is provided at the extreme proximal end of the stylet. The shape of the stylet is typically long and straight but shown in FIG. 2 conforms with the shape of the catheter 10 shown in FIG. 1, for illustrative purposes only. The clinician is capable of twisting the stylet, so that its caudal/distal end when placed inside and to the internal end of the catheter, turns the caudal/distal end of the catheter to navigate various passages and apertures within the patient body. This twisting of the stylet is not recommended but recognises a clinical practice noted in the literature.

Figure 3:
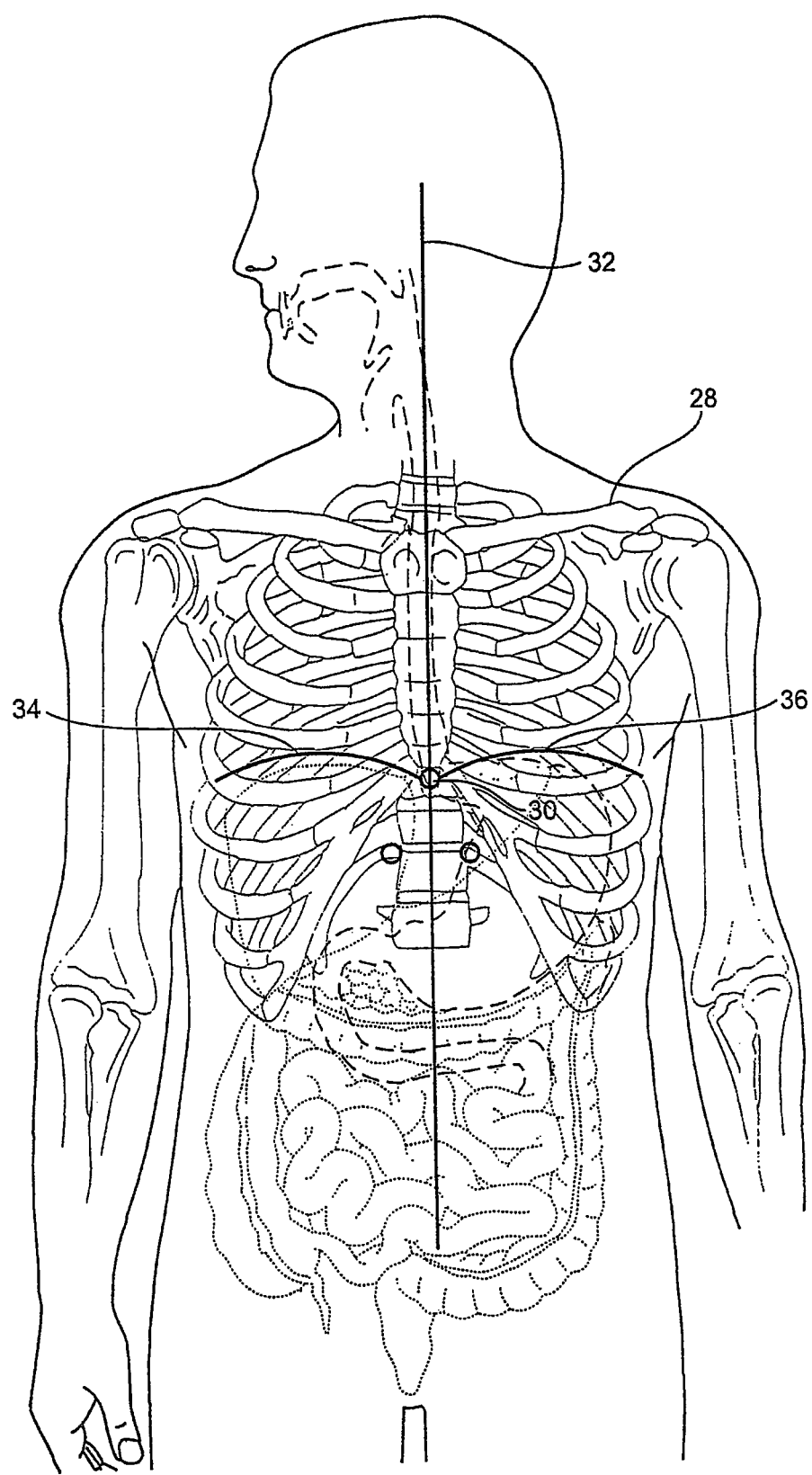
FIG. 3 depicts a detector apparatus positioned appropriately on a patient and an outline of a display that delineates regions of the body.

FIG. 3 depicts an anterior view of the skeleton 28 of a patient and marked in overlay are three circles representative of the preferred location of the three detector coils of the detector apparatus over the patient's body.

The external shape of the detector apparatus is of little consequence to the way in which the actual detector works but it is considered advantageous by the inventors that the external shape helps the clinician to appropriately locate the detector device on or over a predetermined location of the patient. For example a triangular shape places the upper apex of the apparatus towards the head of the patient and the longitudinal axis of the apparatus can be made to lie coincident with the mid-sagittal line of the patient 32.

Circle 30 can be the most important of the three detector coil portions as in this embodiment for the placement of the catheter in the alimentary canal (being that portion of the digestive system of the body, including without limitation, the mucus membrane-lined tube extending from the mouth to the anus including the pharynx, esophagus, stomach and the intestines) or in particular in the intestinal tract, it is positioned directly over the xiphoid sternal junction. This will also place the longitudinal axis of the three detector coils coincident with the median antero-posterior plane 32 of the body (mid-sagittal line). The longitudinal axis of the three detector coils is engraved on to the case of the detector housing for the convenience of the clinician to facilitate ease of positioning particularly since the xiphoid sternal junction is typically easily palpitated.

The xiphoid sternal junction is the point at which the diaphragm is connected to the human skeleton. The two arched lines (34 and 36) shown on the figure, are representative of the upper limits of the quite complex domes of the musculo-membranous partition (diaphragm) separating the abdominal and thoracic cavities and which serves as a major thoracic muscle.

Figure 5:
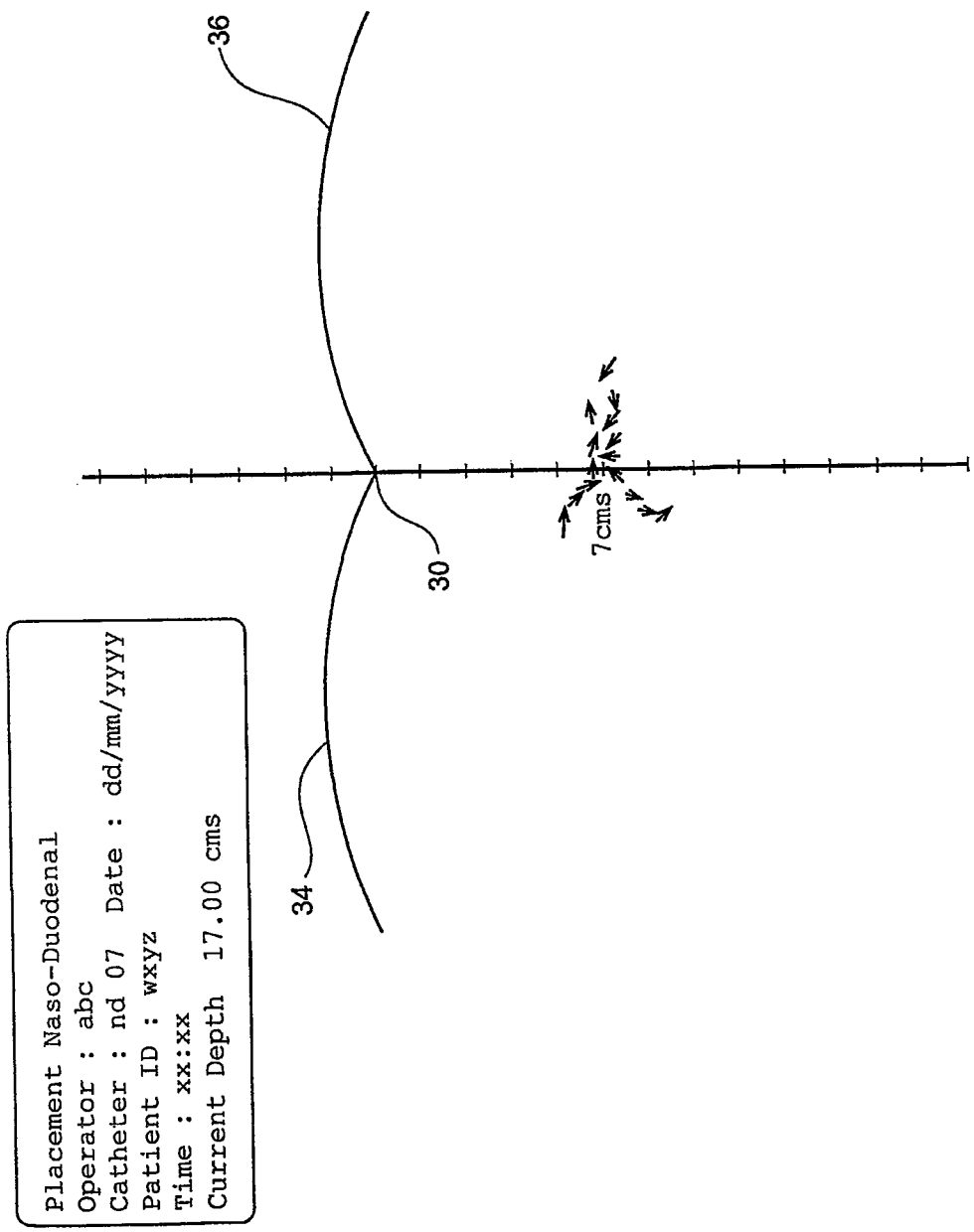
FIG. 5 depicts a typical display only of the coil position located in the stomach of a patient over time even while it is not being moved into a desired location.
Figure 6:
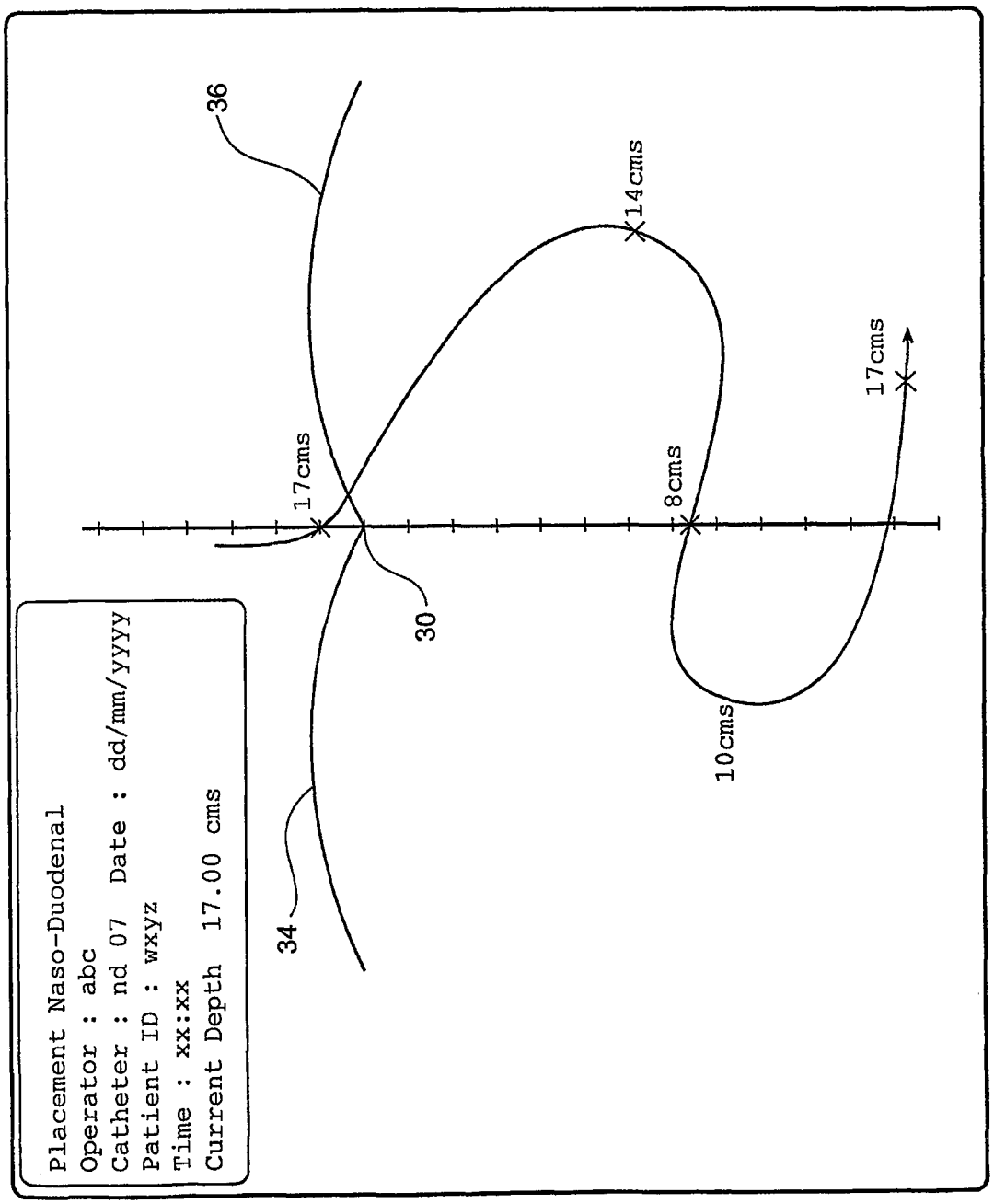
FIG. 6 depicts the recorded path and the current location of a catheter in a patient as would be displayed.

It is of assistance to the clinician that these two arched lines, 34 and 36, are displayed on the monitor along with the mid-sagittal line 32 as is depicted in FIGS. 5 and 6, while the catheter is being located.

The display of the arched lines, 34 and 36 is a tangible consequence of the correct positioning of the detector coils in the manner described. The correlation of the position of the coil in circle 30 with the xiphoid sternal junction allows the monitor to depict the position and depth of the coil with reference to a position of the body that can be found on all patients. It is not imperative that the coil be coincident with that particular bony landmark since the detector apparatus can accommodate any predetermined offset created by having the outer housing of the apparatus located in a particular way that places the coil 30 other than on or over the xiphoid sternal junction.

The device is relatively effective even if the specific coil 30 is not placed precisely in the manner described. It is more important that the two or more signal detector elements are located on or over a part of the human body with reference to a predetermined part or position of the human body. Thus when the position of the coil on the end of the guide wire or catheter is displayed it can be displayed with reference to the approximate position of a known body part or portion so as to assist the clinician during the placement process.

Clearly, the two arched lines 34 and 36 are only representations of the quite complex shape of the diaphragm. Since there is coincidence of at least a portion of the representations with the attachment point of the diaphragm at the xiphoid sternal junction, the lines will be sufficiently accurately depicted on the monitor to assist the clinician. With reference to the measurements taken by the sensor, the representation is an acceptable guide so as to provide confidence to the clinician that at least the caudal/distal end of the catheter is either below or above the diaphragm. Similar representations of parts or portions of the human body could be represented on a monitor referenced to the predetermined positioning of the detector coils.

As in most cases of intestinal intubation, once the caudal/distal end of the catheter/stylet is displayed as passing below the two arches that represent the shape of the diaphragm, the clinician can be sure that the catheter is in the gastrointestinal tract rather than in the airways and/or lung of the patient. Indeed, if the caudal/distal end of the catheter were to be mistakenly routed into the lung, the path of the catheter's caudal/distal end would be shown on the monitor to deviate from that expected.

Figure 4:
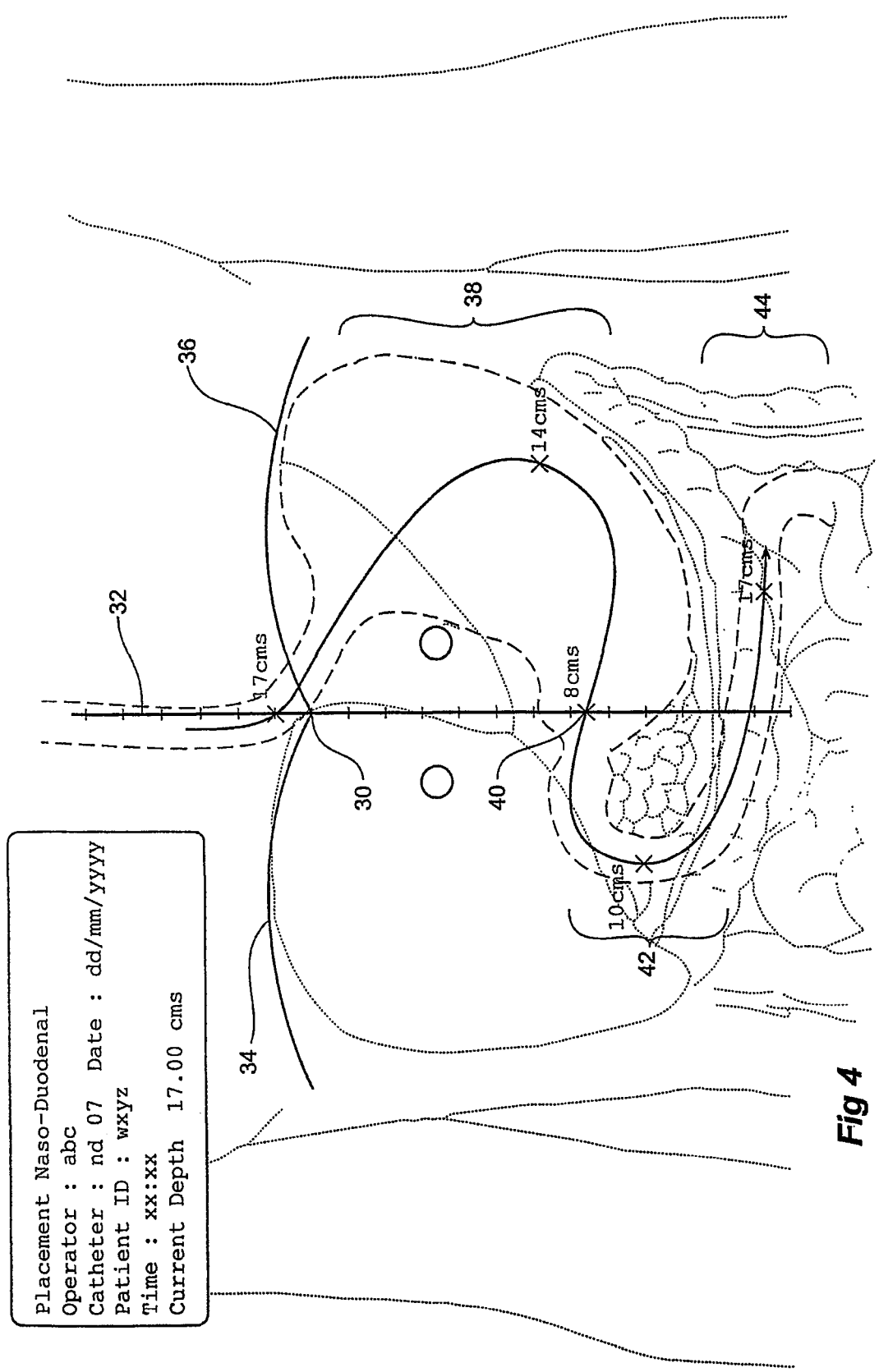
FIG. 4 depicts a display of the location and depth of a coil on the tip of a catheter or stylet superimposed over a representation of a patient.

The first noticeable deviation from the expected route would occur some 10-cm above the two arches. That is, above the xiphoid sternal junction, at the level of the bifurcation of the trachea. This would also be measured as being deeper in the body from that which is expected of the correct route. Since the route shown in FIG. 4 is as expected for an intestinal intubation, it is on track to enter the stomach shown, in general, as region 38. The catheter will then move medially and cross the mid-sagittal line again at 40 entering the first part of the duodenum region 42 through the pylorus orifice. Once through the duodenum region 42, the catheter passes into the jejunum region 44 that is the portion of the small intestine, which extends from the duodenum to the ileum.

It is also possible for the detection method and apparatus to be used to locate particular portions of the catheter. For example, a dual cavity catheter that is used for enteral feeding at its distal end and decompression of gasses in the stomach along it length should ideally have the caudal/distal end located in the jejunum and the decompression cavity extend no further that the pylorus orifice. If the decompression cavity of the catheter begins a known distance from the distal end of the catheter then a stylet having a coil on its end can be drawn back from the distal end of the catheter that known distance. The position of the radiating coil can then be detected and compared with expected position measurements that will indicate whether the catheter is correctly positioned in the patient.

In another example, it will be advantageous to determine whether aspiration or pressure measurement ports located along the length of a catheter are located at the desired position within the body of the patient. This is the case not only at the time of intubation but also during the time the catheter is being used.

The advantage of having a reference point or points on the monitor, which correlates with an actual point, region or structure of the patient, is clearly apparent. This feature is useful during intestinal intubation but it is just as useful when locating a Venous Access Catheter (VAC) which is a generic expression for the better known Central Venous Catheters (CVCs) some of which and their placement will be described in detail later in this specification.

The monitoring of the passage of the catheter through the body and rechecking of correct location during treatment is enabled by means of the catheter locating apparatus described herein. Advantageously, there is less erratic movement of the caudal/distal end of a VAC/CVC as it is placed into location in the upper thoracic region because it is not directly in contact with internal organs of the body that move. Movement caused by the breathing of the patient also affects the display of the position of the catheter tip, much less in this application.

A monitor display that provides lines or a symbol (representative of let us say, the diaphragm) assists the clinician and increases their confidence that the correct path and final position of the caudal/distal end of the catheter has been achieved. However, the positioning of the detector coils in relation to a predetermined reference point is important so that the lines or symbol displayed are correctly positioned relative to the trace and properly reflect the position of the catheter in the body of the patient.

In the case of inserting CVCs with any of the catheter types or methods previously described, it is preferable to position the detector apparatus over a well-defined, preferably bony landmark. In this example, a predetermined one of the three detector coils of the detector apparatus is located over such a landmark. In the particular case of locating the caudal/distal end of a Central Venous Catheter into the superior vena cava of a patient, it is preferable to locate coil 30, as depicted in FIG. 8, on the caudal/mid sagittal aspect of the jugular sternal notch that lies along the mid sagittal line.

Figure 8:
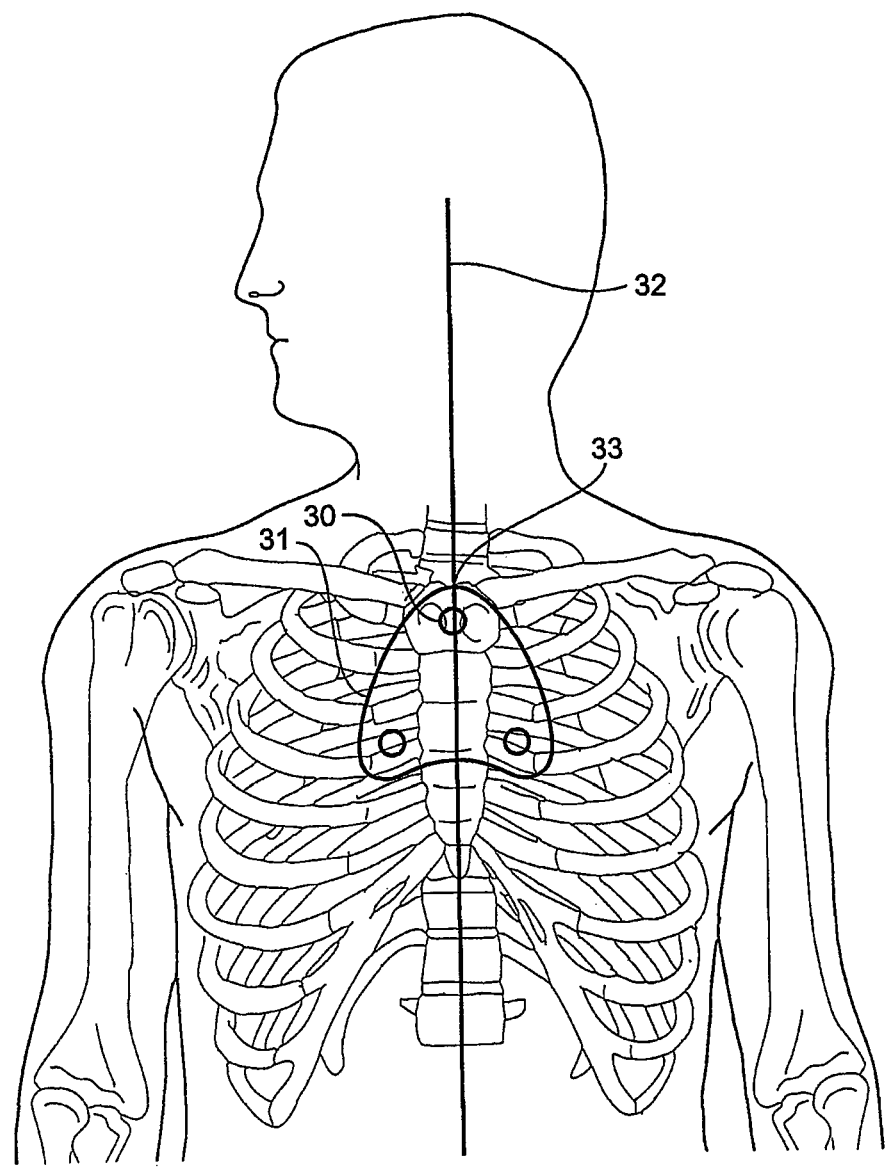
FIG. 8 depicts an outline of a coil location device located in a preferred manner over the caudal/mid sagital aspect of the jugular sternal notch of a patient.

A possible detector apparatus shape 31 is also shown in FIG. 8. The shape of the apparatus is of triangular form in plan view and is preferable for its use on the chest of a patient as described previously. This shape is convenient for the clinician to use because its apex 33 can be located on the caudal/mid sagital aspect of the jugular sternal notch and its longitudinal axis made coincident with the midsagittal line 32 of the patient.

As an aid to the preferable positioning of the detector apparatus, the external casing of the apparatus is preferably marked near its lower corners "LEFT" and "RIGHT" respectively (not shown) ensuring a preferred orientation of this particular shape of apparatus in relation to the patient. Additionally, it is useful to have a line marked or engraved on the apparatus that runs along its longitudinal axis for assisting the visual alignment of that line with the mid sagital line of the patient. However, it would be possible to have a differently shaped detector housing to suit other locations of use on the human body, whether that is for general use or adapted for patient specific reasons.

The caudal/mid sagital aspect of the jugular sternal notch appears to be an ideal point on the body for positioning of the detector apparatus by clinicians as it is common to all humans and readily located visually or palpitated regardless of the physical presentation of the patient. However, the use of the jugular sternal notch as a bony anatomy landmark is not the only bony point or region of the body that could be used for this purpose. There may be other points of the body to which the measuring equipment can be reliably co-located or located with a predetermined offset. Such an arrangement allows the monitor to be used to display a reference point or object, preferably shaped the same as a part of the body that will be useful to the clinician. Such as when intubating a catheter or guide wire or checking the location of a previously located catheter into which a stylet is located and retracted from.

The paths of the catheter/guide wire for enteral or CVC applications are shown in FIGS. 4, 6 as well as 9 and 10 respectively. These paths are ideally represented paths. They are not what is necessarily seen by the clinician while using the locator apparatus during the process of intubation of a catheter for enteral feeding or CVC positioning.

In practice the current position and depth of the signal emitting coil is displayed in a manner more like that shown in FIG. 5.

The coil at the caudal/distal end of the enteral feeding catheter when used in certain body regions of a living patient will be subjected to continual movement due to the involuntary movement of the internal organs of the patient. This can be due to the simple act of breathing (movement of the diaphragm). It can also be due to peristalsis (movement by the tubular organs such as the stomach, duodenum and jejunum in which both longitudinal and circular muscle fibres of those organs propel their contents). Furthermore there are other unavoidable movements that occur during the intubation procedure, although the extent of movement is much less for intubation into organs of the upper thoracic cavity Clearly, to provide the most useful form of display there needs to be a balance between the delay between drawing successive arrows (which represent the current position, depth and orientation of the coil) and the need to display the movement of the coil to the clinician. Too long an interval may allow the coil to traverse an unacceptable distance along an incorrect path before it is recorded on the screen and displayed to the clinician. Too short an interval merely fills the screen with arrows that appear to jump about due to the movement factors described above. Either of these cases may confuse or mislead the clinician rather than being of assistance.

The ideal delay is ultimately a matter of clinical preference and the apparatus can be adjusted by the clinician to deliver/provide a desired display characteristics. Such a delay may be different when CVC catheters are being inserted or being inserted into other regions of the body.

The quantity of successively displayed location indicia is also a matter for clinical preference and in the example shown in FIG. 5 there are 14 successive positions shown at any one time. The tail of the display disappears as the route of the coil progresses through the internal organs of a patient so as to keep to a minimum the number of indicia on the screen at any one time. The monitor would otherwise become cluttered with symbols, which would make it difficult to discern the relevant movement and location of the current position of the caudal/distal end of the catheter/guide wire. Use of different colours to represent the newest versus the last and intermediate indicators is also contemplated to be advantageous to the clinician.

With regard to an enteral feeding catheter, once the caudal/distal end of the catheter is located in the area of the jejunum, a location most suitable for enteral tube feeding, the guide wire can be retracted. At this point the location and depth detection equipment can be used in a recording mode.

If the guide wire is retracted over a period of say three seconds, the monitor will be used to trace the path (X-Y and depth) of the coil as it passes back through the route of the then properly located catheter. The detector apparatus is arranged to record the radial distance of the radiating coil from the two or more detector coils at predetermined intervals suitable for providing enough measurements to calculate a line of best fit. Clearly the more measurements the better the line of best fit will be. There are however, many techniques for transforming such measurements into a visual indicator of the route of the coil as it is retracted from the catheter. Those skilled in the electronic and computing arts would readily be able to provide such functionality.

The change in the signal detected can be used to determine the path being taken by the radiating coil and there exist many other ways in which the activity of the coil can be detected and processed to be displayed. A further way would be to display the coil position each time there is a predetermined change. The actual change required would be controllable by the user to suit the type of use the radiating coil was being put to at the time.

A processor having computer functions would be one of many ways of performing the comparisons of various signals received by the detector device, that as is disclosed in the referred to US patent by the applicants, comprises three coils set in a particular spatial relationship.

The processor would produce indicator data based on the signals received and processed by the processor. The processor can then also produce indicator data representative of the position of the radiating coil in the form most useful to the user of the apparatus. One such form is an indicator image. The figures display an arrow symbol that is an indication to the user of the position and direction of the coil being detected. This particular indicator image is useful but there will be many as useful alternatives.

The processor will also be capable of producing reference data that specifies a predetermined reference image. The reference image could be that of any line, curve or object. Preferably, the reference image is that of an appropriate part or portion of a body. That part or portion is not the actual part or portion of the patient being intubated but rather a created pictorial representation of such. In particular it could be of a non-subject body (that is not the patient). As stated previously, it is intended that different types of catheter locating apparatus be made to be incompatible it may be possible to use a common detector device. However, in the case of there being different devices it may not be necessary for them to provide any indication to the processor of their type. Since the two would be made for each other it may be possible for a data storage device containing one or more predetermined reference images to be available. Thus the data storage device can be used to provide an appropriate image of say a sternum for the type of detector device and its location being used. The data storage device can also provide storage for symbols and other images useful in displaying information on a display relating to the position of a radiating coil (indicator data) used with a catheter and a reference image (an appropriately located symbol of a point or part of a body).

The display shown in FIG. 6 is a typical result, which shows a trace in a particular patient. Other patients may display a slightly different path and depth. The depth measurements shown is a relative measure and not an absolute, but used in the appropriate way it can greatly assist trained and experienced personnel intubating a catheter into a patient.

Thus the relative depths of the tip of the catheter are taken greatest note of since the ratio of change from person to person will very likely be small.

In an example of an enteral feeding catheter intubation the display shown in FIG. 6 shows that when the catheter passes below the xiphoid sternal junction 30 it is very deep (say 17 cms below the location of the detector device). While the catheter passes through the stomach, its tip lies closer and less deep (say 14 cms) and when passing under the mid sagital line 32 it is very shallow and closest to the surface of the patient (say 8 cms). In the first part of the duodenum it is relatively shallow (say 10 cms) and finally becomes very deep (say 17 cms) when in the duodenum/jejunum.

After long term clinical use, an acceptable and reliable range of depths and ratios at the points or regions described above (or others) will be developed and most useful for assisting clinical assessment of the correctness of the route taken by the catheter. Again, it can be seen that although not proof of the exact location of the caudal/distal end of the stylet mounted coil and hence the tip of the catheter, the displayed characteristics provide yet another aid to improving clinical decision making in respect of the location of a catheter.

A stylet is capable of being reused in a catheter (after decontamination and cleaning). Thus, it can be cheaper to use in a clinical environment and encourages more frequent checking of the catheter location than would otherwise be the case because the expense and time consuming nature of X-ray or other detection methods. Stylet reuse, although common in the clinical environment, is not recommended by the authors of this document, until there is regulatory approval under a code of practice governing re-use of such devices.

It should not of course be forgotten that other clinical monitoring techniques should continue to be used thereby increasing the confidence of the clinician that the catheter is appropriately located, whether that be for enteral/parenteral nutrition or other purposes.

Patients are often intubated with VAC/CVCs using image guidance by means of X-rays, fluoroscopy and ultrasonography. Percutaneous central venous access is achieved when the tip of a catheter is located in the caval atrial region. Tunneled catheters travel through a subcutaneous tract prior to exiting the body via an incision in the skin. Such catheters are used for medicament delivery and dialysis. Image-guided techniques, although expensive, are less fraught with early complications than blind or external landmark intubation techniques.

VAC/CVCs are now used for long-term intravenous antibiotic support as well as parenteral nutritional support and blood sampling.

A selection from the many types of VAC/CVC in the marketplace can include single- or multi-lumen short-term "central lines", tunneled catheters, such as Hickman™ or Groshong™, and implanted catheters, such as PortACath™ or InfusaPort™. In addition, Peripherally Inserted Central Catheters (PICCs) are also available.

The invention described herein can assist in the correct placement of most catheters and most advantageously can be used to check and confirm their correct placement at any time following initial placement.

Figure 7:
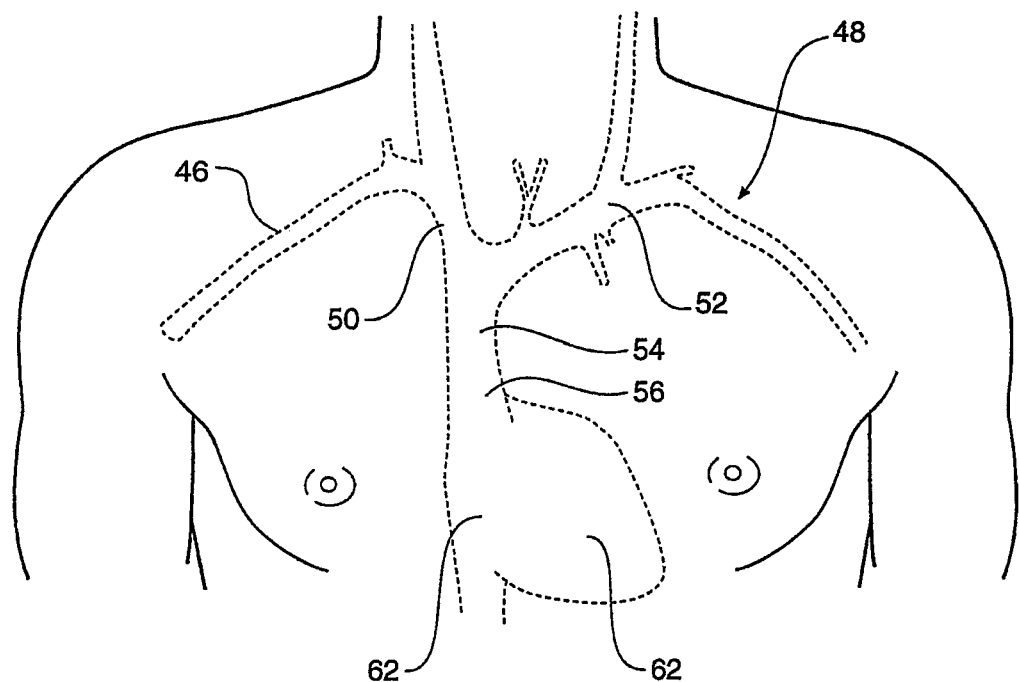
FIG. 7 depicts the venous system of the upper torso.

FIG. 7 depicts an anterior view of the venous system of the upper torso showing the right subclavian vein 46 and the left subclavian vein 48 which meet medially with corresponding right and left brachiocephalic veins 50 and 52 respectively.

The junction of the brachiocephalic veins occurs at the upper region of the superior vena cava 54, which descends towards the cavoatrial junction 56 prior to entering the right atrium 60 of the heart 62.

Figure 9:
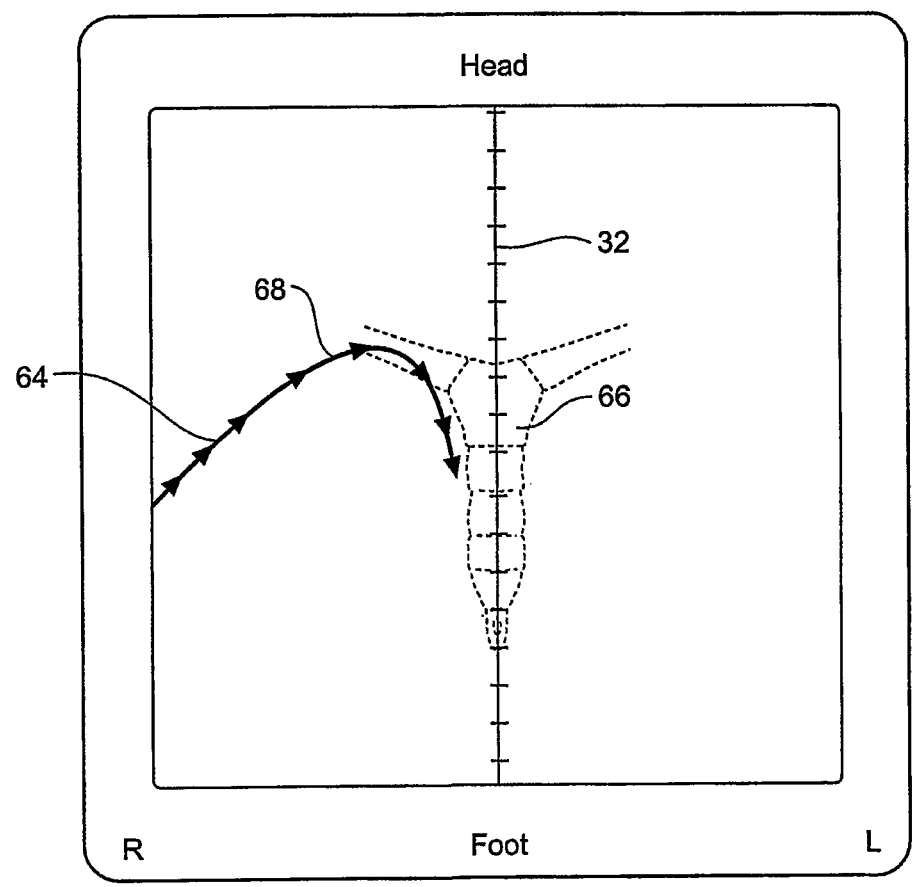
FIG. 9 depicts a pictorial representation of a correctly placed Central Venous Catheter (CVC) in the superior vena cava of a patient.

FIG. 9 depicts, as would be seen on a screen visible to the clinician, a constructed trace 64 of the path of a Peripherally Inserted Central Catheter (PICC) which has its tip ideally located in the central region of the superior vena cava 54. FIG. 9 also depicts an outline of a sternum 66 thus providing a region of reference for the clinician between what is shown on screen and a known landmark of the patient's body. Clearly, the outline is a pictorial representation of a generic sternum and not the sternum of the patient. This representation is, in any event, useful to the clinician for the task at hand.

During placement of the PICC, because of the relative stability of the organs above the diaphragm of the patient, the feed in trace provided on a monitor will be similar to the pull back trace described in respect of enteral feeding catheters. It will be clear that the tip of the catheter has entered the superior vena cava from not only the two dimensional route displayed on the monitor, but also confirmed by its depth as it wends its way through the various branches of the venous system in the upper torso of the patient while being feed over the previously inserted guide wire.

Most obvious to the clinician from the monitor will be the sharp change in direction and relevant depth of the catheter as it transitions from the subclavian vein into the brachiocephalic vein (68 of FIG. 9).

As described previously, an independently identified measure of the most preferred location of the tip of the catheter occurs when, in an adult, there is about 9 cm of linear distance between the catheter tip and the appropriately located measuring instrument. This is with reference to when a detector apparatus has been placed on the caudal/mid sagital aspect of the jugular sternal notch along the midsagittal line of the patient.

Such an explicit measurement is used herein as an example only, of the practical methodology associated with the use of the device but it may well not be totally accurate for all circumstances. Such measurements though, are likely as described previously, to become clinically acceptable as an indicator of the appropriate location of the tip of the catheter as the number of patients measured increases and verification by other methods occur and further data is gathered and analyzed in the future.

The display is particularly useful to the clinician as the progress of the tip of the catheter is continuous and always displayed with reference to, in this embodiment, the position of the patient's sternum as is indicated by the shape 66 on the monitor display.

Figure 10:
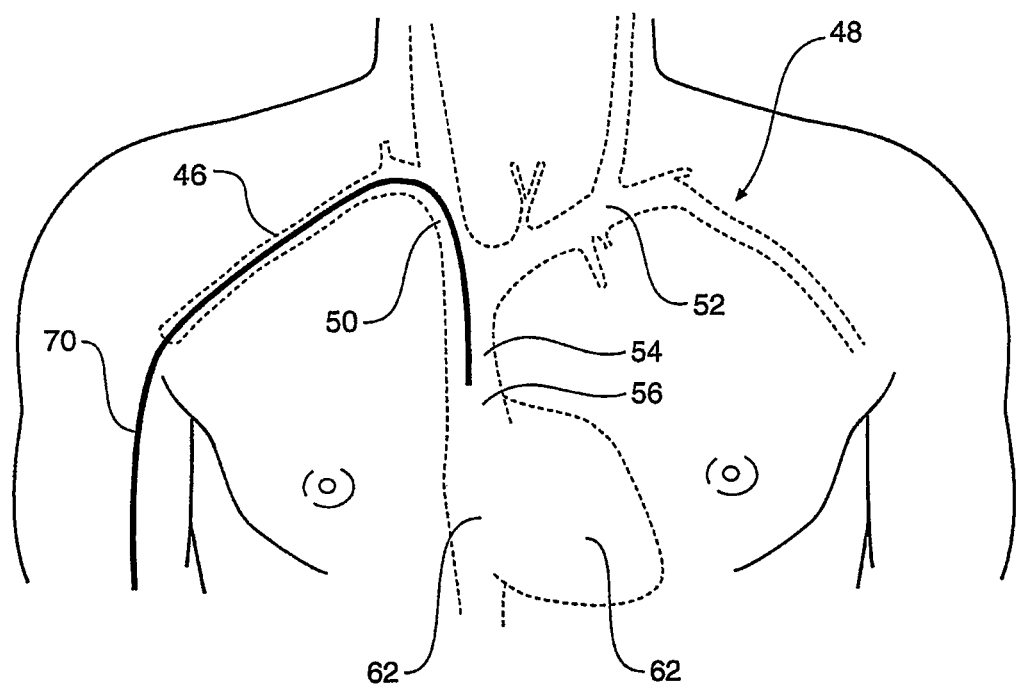
FIG. 10 depicts a pictorial representation of the upper torso of a patient showing the path of a CVC and its tip in the region of the superior vena cava.

FIG. 10 depicts some of the venous system of the upper thoracic cavity and in particular the placement of a PICC 70 terminating in the superior vena cava.

It should be apparent from the foregoing that the part or portion of the body displayed is not used to explicitly locate the signal radiating coil with reference to it but is used more as a guide.

The clinician will learn from their observations over time that the position of the inserted coil as determined by the signal detectors indicates a radial distance of X cms relative to a predetermined location on the signal detector apparatus and not the displayed symbol. The processor will be capable of providing the coordinates, in say X and Y in the horizontal plane (assuming a supine patient) of the location of the coil both as an image on the screen but also in figures.

When the signal detector apparatus itself is consistently located with reference to a predetermined body part or portion thereof, each measurement displayed will be referenced to the displayed reference image. However, this is not meant to be an absolute and what the clinician experiences and assesses as the actual position in say a particular organ or channel in the body is a matter of acquired expertise.

Thus the display is used on two levels. One is to provide accurate radial distance X or (X,Y) from a predetermined point on the detector apparatus. The other is to reference that position measurement to a known body part or portion thereof (that might be a different one to that displayed).

The body part or portion displayed is only pictorial. It is only used as an indicator of a region.

The arched lines (depicted in FIGS. 3, 4 and 5) represent as discussed previously the complex shape on a vertical cross-section of the diaphragm of a typical human. Since the electronics used in the detector apparatus and the display expect that the upper coil of the detector coils has been placed on a particular bony landmark, the display can show the position the junction of the two curved lines and reference the measurements of the position of the catheter coil accordingly.

It is thus possible, even recognizing that the display is only an indicator, to provide prompts additional to the obvious visual ones. These prompts may inform the clinician that the signal-radiating coil is above or below the arched line indicative of the diaphragm of the patient. These prompts could be in the form of audible signals.

Say for example, audible tones may increase in frequency as the depicted coil position gets closer from above the arched lines assuming that the head end of the patient is correctly determined by correct placement of the detector device. Furthermore, as the coil position displayed moves below and a way from the displayed arched lines an audible tone may pluses less quickly the further it moves away.

The audible signals could be of a type that is preferable to the user of the apparatus.

It is also possible for the measured position to be used to indicate the possibility of an incorrect placement. This requires the equivalent of an expert system information database to be programmed into the display device. Ideally, for a predetermined location of the signal detector apparatus on the body, there are defined regions in the body consisting of certain radial distances from the signal detector, that if measured during an intubation would indicate that the signal radiating coil is in or approaching an undesirable region or part of the body.

Thus not only does the clinician form over time a feel for the expected position measurements but the expert system can be used as a backup to warn the clinician of the progression of the radiating coil and thus the catheter into an inappropriate region of the patient. This further indication can be by way of visual indicators on the monitor screen or by additional audible signals. Recognizing that there are variations in the anatomy of the human body from patient to patient, it is important to note that the method described provides guidance and is no substitute for clinical experience.

As clinical experience accumulates with the placement of catheters in other parts of the body, it will be possible to overlay on a monitor other reference images such as representations of static points, regions, or structures of the anatomy that may assist the clinician. Additional visual and audible information can also provide guidance to the skilled clinician or registered nurse authorised to locate catheters into patients.

It will be appreciated by those skilled in the art, that the invention is not restricted in its use to the particular application described. Neither is the present invention restricted in its preferred embodiment with regard to the particular elements and/or features described or depicted herein. It will be appreciated that various modifications can be made without departing from the principles of the invention. Therefore, the invention should be understood to include all such modifications within its scope.

What is claimed is:

1. A method of controlling a display device for confirming placement of a catheter inserted into a subject after the catheter is inserted through a nasal or oral cavity of the subject, wherein the catheter has a tip positioned in a jejunum of the subject, the method comprising:
    (a) storing data representative of a reference image in a data storage device;
    (b) displaying on the display device the reference image, the reference image including:
        (i) a vertical line representing a mid-sagittal line of the subject, and
        (ii) a horizontal line representing a vertical cross-section of a diaphragm of the subject, wherein the vertical line and horizontal line intersect at a point representative of a xiphoid process of the subject;
    (c) storing instructions which, when executed by a processor, cause the processor to generate a graphical representation of an insertion path of the catheter, which includes a coil inserted into the catheter that is detected by a detector positioned over a predetermined location of an anterior surface of the subject for detecting a position of the coil; and
    (d) displaying on the display device, in three-dimensions, the graphical representation of an insertion path of the catheter,
    wherein confirmation of placement of the catheter in the subject is enabled based on the graphical representation of the insertion path, and
    wherein the graphical representation of the insertion path defines a shape including:
        (i) an esophageal segment extending substantially parallel to said vertical line, the esophageal segment extending from a position above the horizontal line to the horizontal line and having a first depth relative to the anterior surface of the subject, the esophageal segment indicating absence of placement in an airway of the subject,
        (ii) a stomach segment extending from said vertical line abaxially away from the vertical line, returning axially to the vertical line and having a second depth relative to the anterior surface of the subject,
        (iii) a pylorus segment intersecting the vertical line at a third depth relative to the anterior surface of the subject,
        (iv) a duodenum segment extending abaxially away from the vertical line in a direction substantially opposite from the stomach segment, returning axially to the vertical line and having a fourth depth relative to the anterior surface of the subject, and
        (v) a jejunum segment extending abaxially away from said vertical line in a direction substantially opposite the duodenum segment, the jejunum segment terminating in a location representing the jejunum of the subject.

2. The method of claim 1, wherein the second depth is shallower than the first depth.

3. The method of claim 1, wherein the third depth is shallower than both the second depth and the first depth.

4. The method of claim 1, wherein the fourth depth is deeper than the third depth.

5. The method of claim 1, wherein the fourth depth is deeper than the third depth and the third depth is shallower than the first depth.

6. The method of claim 1, wherein the esophageal segment has a range of depths relative to the anterior surface of the subject, and wherein the first depth represents a maximum depth of said esophageal segment in said range.

7. The method of claim 1, wherein the stomach segment has a range of different depths relative to the anterior surface of the subject, and wherein the second depth represents a maximum depth of said stomach segment in said range.

8. The method of claim 1, wherein the pylorus segment has a range of different depths relative to the anterior surface of the subject, and wherein the third depth represents a minimum depth of said pylorus segment in said range.

9. The method of claim 1, wherein the duodenum segment has a range of different depths relative to the anterior surface of the subject, and wherein the fourth depth represents a maximum depth of said duodenum segment in said range.

10. A method of controlling a display device for confirming placement of a catheter inserted into a subject, after the catheter is inserted through a nasal or oral cavity of the subject, wherein the catheter has a tip positioned in a stomach of the subject, the method comprising:
    (a) storing data representative of a reference image in a data storage device;
    (b) displaying on the display device the reference image, the reference image including:
        (i) a vertical line representing a mid-sagittal line of the subject, and
        (ii) a horizontal line representing a vertical cross-section of a diaphragm of the subject;
    (c) storing instructions which, when executed by a processor, cause the processor to generate a graphical representation of an insertion path of the catheter, which includes a coil inserted into the catheter that is detected by a detector positioned over a predetermined location of an anterior surface of the subject for detecting a position of the coil; and
    (d) displaying on the display device, in three-dimensions, the graphical representation of an insertion path of the catheter,
    wherein confirmation of placement of the catheter in the subject is enabled based on the graphical representation of the insertion path, and
        wherein the graphical representation of the insertion path defines a shape including:
            (i) an esophageal segment extending substantially parallel to said vertical line, the esophageal segment extending from a position above the horizontal line to the horizontal line and having a first depth relative to the anterior surface of the subject, the esophageal segment indicating absence of placement in an airway of the subject, and
            (ii) a stomach segment extending from said vertical line abaxially away from the vertical line, returning axially to the vertical line and having a second depth relative to the anterior surface of the subject, the stomach segment terminating in a location representing the stomach of the subject.

11. The method of claim 10, which includes displaying the stomach segment terminating in the stomach of the subject at a second depth relative to the surface of the subject, wherein the second depth is shallower than the first depth.

12. The method of claim 11, wherein the esophageal segment has a range of depths relative to the anterior surface of the subject, and wherein the first depth represents a maximum depth of said esophageal segment in said range.

13. The method of claim 11, wherein the stomach segment has a range of different depths relative to the anterior surface of the subject, and wherein the second depth represents a maximum depth of said stomach segment in said range.

14. A method of controlling a display device for confirming placement of a catheter inserted into a subject, after the catheter is inserted through a nasal or oral cavity of a subject, wherein the catheter has a tip positioned in a duodenum of the subject, the method comprising:
    (a) storing data representative of a reference image in a data storage device;
    (b) displaying on the display device the reference image, the reference image including:
        (i) a vertical line representing a mid-sagittal line of the subject, and
        (ii) a horizontal line representing a vertical cross-section of a diaphragm of the subject;
    (c) storing instructions which, when executed by a processor, cause the processor to generate a graphical representation of an insertion path of the catheter, which includes a coil inserted into the catheter that is detected by a detector positioned over a predetermined location of an anterior surface of the subject for detecting a position of the coil; and
    (d) displaying on the display device, in three-dimensions, the graphical representation of an insertion path of the catheter,
    wherein confirmation of placement of the catheter in the subject based on the graphical representation of the insertion path, and
        wherein the graphical representation of the insertion path defines a shape including:
            (i) an esophageal segment extending substantially parallel to said vertical line, the esophageal segment extending from a position above the horizontal line to the horizontal line and having a first depth relative to the anterior surface of the subject, the esophageal segment indicating absence of placement in an airway of the subject,
            (ii) a stomach segment extending from said vertical line abaxially away from the vertical line, returning axially to the vertical line and having a second depth relative to the anterior surface of the subject,
            (iii) a pylorus segment intersecting the vertical line at a third depth relative to the anterior surface of the subject, and
            (iv) a duodenum segment extending abaxially away from the vertical line in a direction substantially opposite from the stomach segment, returning axially to the vertical line and having a fourth depth relative to the anterior surface of the subject.

15. The method of claim 14, wherein the second depth is shallower than the first depth.

16. The method of claim 14, wherein the third depth is shallower than both the second depth and the first depth.

17. The method of claim 14, wherein the fourth depth is deeper than the third depth.

18. The method of claim 14, wherein the fourth depth is deeper than the third depth and the third depth is shallower than the first depth.

19. The method of claim 14, wherein the esophageal segment has a range of depths relative to the anterior surface of the subject, and wherein the first depth represents a maximum depth of said esophageal segment in said range.

20. The method of claim 14, wherein the stomach segment has a range of different depths relative to the anterior surface of the subject, and wherein the second depth represents a maximum depth of said stomach segment in said range.

21. The method of claim 14, wherein the pylorus segment has a range of different depths relative to the anterior surface of the subject, and wherein the third depth represents a minimum depth of said pylorus segment in said range.

22. The method of claim 14, wherein the duodenum segment has a range of different depths relative to the anterior surface of the subject, and wherein the fourth depth represents a maximum depth of said duodenum segment in said range.

23. A method of controlling a display device for confirming intubation of a catheter in a human subject, wherein the catheter is inserted through a nasal or oral cavity of the subject, the method comprising:
(a) storing data representative of a reference image in a data storage device;
(b) displaying on the display device the reference image, the reference image including:
  (i) a vertical line representing a mid-sagittal line of the subject, and
  (ii) a horizontal line representing a vertical cross-section of a diaphragm of the subject;
(c) storing instructions which, when executed by a processor, cause the processor to generate a graphical representation of an insertion path of the catheter, which includes a coil inserted into the catheter that is detected by a detector positioned over a predetermined location of an anterior surface of the subject for detecting a position of the coil;
(d) at a first time, detecting a distal end of the catheter at a first location in the subject;
(e) in response to the distal end of the catheter being at the first location in the subject, displaying, in three-dimensions, a graphical representation of the distal end of the catheter at a first position of the displayed reference image, the first position of the displayed reference image located along the vertical line of the displayed reference image and having a first depth relative to the anterior surface of the subject;
(f) at a second time, detecting the distal end of the catheter at a second location in the subject, the second location representing a stomach of the subject;
(g) in response to the distal end of the catheter being at the second location in the subject, displaying, in three-dimensions, a graphical representation of the distal end of the catheter at a second position of the displayed reference image, the second position having a second depth relative to the anterior surface of the subject;
(h) at a third time, detecting the distal end of the catheter at a third location in the subject;
(i) in response to the distal end of the catheter being at the third location in the subject, displaying, in three-dimensions, a graphical representation of the distal end of the catheter at a third position of the displayed reference image, the third position of the displayed reference image located along the vertical line of the displayed reference image and having a third depth relative to the anterior surface of the subject;
(j) at a fourth time, detecting the distal end of the catheter at a fourth location representing a duodenum of the subject;
(k) in response to the distal end of the catheter being at the fourth location in the subject, displaying, in three-dimensions, a graphical representation of the distal end of the catheter at a fourth position of the displayed reference image, the fourth position having a fourth depth relative to the anterior surface of the subject;
(l) at a fifth time, detecting the distal end of the catheter at a fifth location in the subject, the fifth location representing a jejunum of the subject; and
(m) in response to the distal end of the catheter being at the fifth location in the subject, displaying, in three-dimensions, a graphical representation of the distal end of the catheter at a fifth position of the displayed reference image,
wherein confirmation of an insertion path of the catheter, in three-dimensions, is enabled based on the graphical representation of the distal end of the catheter at each of the first, second, third, fourth, and fifth positions of the reference image.

24. A method of controlling a display device for confirming intubation of a catheter in a human subject, wherein the catheter is inserted through a nasal or oral cavity of the subject, the method comprising:
(a) storing data representative of a reference image in a data storage device;
(b) displaying on the display device the reference image, the reference image including:
  (i) a vertical line representing a mid-sagittal line of the subject, and
  (ii) a horizontal line representing a vertical cross-section of a diaphragm of the subject;
(c) storing instructions which, when executed by a processor, cause the processor to generate a graphical representation of an insertion path of the catheter, which includes a coil inserted into the catheter that is detected by a detector positioned over a predetermined location of an anterior surface of the subject for detecting a position of the coil;
(d) at a first time, detecting a distal end of the catheter at a first location in the subject;
(e) in response to the distal end of the catheter being at the first location in the subject, displaying, in three-dimensions, a graphical representation of the distal end of the catheter at a first position of the displayed reference image, the first position of the displayed reference image located along the vertical line of the displayed reference image and having a first depth relative to the anterior surface of the subject;
(f) at a second time, detecting the distal end of the catheter at a second location in the subject, the second location representing a stomach of the subject;
(g) in response to the distal end of the catheter being at the second location in the subject, displaying, in three-dimensions, a graphical representation of the distal end of the catheter at a second position of the displayed reference image, the second position having a second depth relative to the anterior surface of the subject;
(h) at a third time, detecting the distal end of the catheter at a third location in the subject;
(i) in response to the distal end of the catheter being at the third location in the subject, displaying, in three-dimensions, a graphical representation of the distal end of the catheter at a third position of the displayed reference image, the third position of the displayed reference image located along the vertical line of the displayed reference image and having a third depth relative to the anterior surface of the subject;
(j) at a fourth time, detecting, the fourth location representing a duodenum of the subject; and
(k) in response to the distal end of the catheter being at the fourth location in the subject, displaying, in three-dimensions, a graphical representation of the distal end of the catheter at a fourth position of the displayed reference image, the fourth position having a fourth depth relative to the anterior surface of the subject,
wherein confirmation of an insertion path of the catheter, in three-dimensions, is enabled based on the graphical representation of the distal end of the catheter at each of the first, second, third, and fourth, positions of the reference image.

25. A method of controlling a display device for confirming intubation of a catheter in a human subject, wherein the catheter is inserted through a nasal or oral cavity of the subject, the method comprising:
   (a) storing data representative of a reference image in a data storage device;
   (b) displaying on the display device the reference image, the reference image including:
      (i) a vertical line representing a mid-sagittal line of the subject, and
      (ii) a horizontal line representing a vertical cross-section of a diaphragm of the subject;
   (c) storing instructions which, when executed by a processor, cause the processor to generate a graphical representation of an insertion path of the catheter, which includes a coil inserted into the catheter that is detected by a detector positioned over a predetermined location of an anterior surface of the subject for detecting a position of the coil;
   (d) at a first time, detecting a distal end of the catheter at a first location in the subject;
   (e) in response to the distal end of the catheter being at the first location in the subject, displaying, in three-dimensions, a graphical representation of the distal end of the catheter at a first position of the displayed reference image, the first position of the displayed reference image located along the vertical line of the displayed reference image and having a first depth relative to the anterior surface of the subject;
   (f) at a second time, detecting the distal end of the catheter at a second location in the subject, the second location representing a stomach of the subject; and
   (g) in response to the distal end of the catheter being at the second location in the subject, displaying, in three-dimensions, a graphical representation of the distal end of the catheter at a second position of the displayed reference image, the second position having a second depth relative to the anterior surface of the subject,
   wherein confirmation of an insertion path of the catheter, in three-dimensions, is enabled based on the graphical representation of the distal end of the catheter at each of the first and second positions of the reference image.

26. A method of controlling a display device for confirming intubation of a catheter in a human subject, wherein the catheter extends through a nasal or oral cavity of the subject and terminates at a jejunum of the subject, the method comprising:
   (a) storing data representative of a reference image in a data storage device;
   (b) displaying on the display device the reference image, the reference image including:
      (i) a vertical line representing a mid-sagittal line of the subject, and
      (ii) a horizontal line representing a vertical cross-section of a diaphragm of the subject;
   (c) storing instructions which, when executed by a processor, cause the processor to generate a graphical representation of an insertion path of the catheter, which includes a coil inserted into the catheter that is detected by a detector positioned over a predetermined location of an anterior surface of the subject for detecting a position of the coil;
   (d) displaying on the display device, in three-dimensions, a graphical representation of a first portion of the catheter at a first position of the displayed reference image, the first position being located along the vertical line of the displayed reference image and having a first depth relative to the anterior surface of the subject;
   (e) displaying on the display device, in three-dimensions, a graphical representation of a second portion of the catheter at a second position of the displayed reference image, the second position representing a stomach of the subject and having a second depth relative to the anterior surface of the subject;
   (f) displaying on the display device, in three-dimensions, a graphical representation of a third portion of the catheter at a third position of the displayed reference image, the third position being located along the vertical line of the displayed reference image and having a third depth relative to the anterior surface of the subject;
   (g) displaying on the display device, in three-dimensions, a graphical representation of a fourth portion of the catheter at a fourth position of the displayed reference image, the fourth position representing a duodenum of the subject and having a fourth depth relative to the anterior surface of the subject; and
   (h) displaying on the display device, in three-dimensions, a graphical representation of a fifth portion of the catheter at a fifth position of the displayed reference image, the fifth position representing the jejunum of the subject,
   wherein confirmation of an insertion path of the catheter, in three-dimensions, is enabled based on the graphical representation of an insertion path of the catheter including:
      (i) the graphical representation of the first portion of the catheter at the first position of the reference image,
      (ii) the graphical representation of the second portion of the catheter at the second position of the reference image,
      (iii) the graphical representation of the third portion of the catheter at the third position of the reference image,
      (iv) the graphical representation of the fourth portion of the catheter at the fourth position of the reference image, and
      (v) the graphical representation of the fifth portion of the catheter at the fifth position of the reference image.

27. A method of controlling a display device for confirming intubation of a catheter in a human subject, wherein the catheter extends through a nasal or oral cavity of the subject and terminates at a jejunum of the subject, the method comprising:
   (a) storing data representative of a reference image in a data storage device;
   (b) displaying on the display device the reference image, the reference image including:
      (i) a vertical line representing a mid-sagittal line of the subject, and
      (ii) a horizontal line representing a vertical cross-section of a diaphragm of the subject;
   (c) storing instructions which, when executed by a processor, cause the processor to generate a graphical representation of an insertion path of the catheter, which includes a coil inserted into the catheter that is detected by a detector positioned over a predetermined location of an anterior surface of the subject for detecting a position of the coil;
   (d) displaying on the display device, in three-dimensions, a graphical representation of a first portion of the catheter at a first position of the displayed reference image, the first position being located along the vertical line of the displayed reference image and having a first depth relative to the anterior surface of the subject;

(e) displaying on the display device, in three-dimensions, a graphical representation of a second portion of the catheter at a second position of the displayed reference image, the second position representing a stomach of the subject and having a second depth relative to the anterior surface of the subject;

(f) displaying on the display device, in three-dimensions, a graphical representation of a third portion of the catheter at a third position of the displayed reference image, the third position being located along the vertical line of the displayed reference image and having a third depth relative to the anterior surface of the subject; and (g) displaying on the display device, in three-dimensions, a graphical representation of a fourth portion of the catheter at a fourth position of the displayed reference image, the fourth position representing a duodenum of the subject and having a fourth depth relative to the anterior surface of the subject, wherein confirmation of an insertion path of the catheter, in three-dimensions, is enabled based on the graphical representation of an insertion path of the catheter including:
  (i) the graphical representation of the first portion of the catheter at the first position of the reference image,
  (ii) the graphical representation of the second portion of the catheter at the second position of the reference image,
  (iii) the graphical representation of the third portion of the catheter at the third position of the reference image, and
  (iv) the graphical representation of the fourth portion of the catheter at the fourth position of the reference image.

28. A method of controlling a display device for confirming intubation of a catheter in a human subject, wherein the catheter extends through a nasal or oral cavity of the subject and terminates at a jejunum of the subject, the method comprising:

(a) storing data representative of a reference image in a data storage device;

(b) displaying on the display device the reference image, the reference image including:
  (i) a vertical line representing a mid-sagittal line of the subject, and
  (ii) a horizontal line representing a vertical cross-section of a diaphragm of the subject;

(c) storing instructions which, when executed by a processor, cause the processor to generate a graphical representation of an insertion path of the catheter, which includes a coil inserted into the catheter that is detected by a detector positioned over a predetermined location of an anterior surface of the subject for detecting a position of the coil;

(d) displaying on the display device, in three-dimensions, a graphical representation of a first portion of the catheter at a first position of the displayed reference image, the first position being located along the vertical line of the displayed reference image and having a first depth relative to the anterior surface of the subject;

(e) displaying on the display device, in three-dimensions, a graphical representation of a second portion of the catheter at a second position of the displayed reference image, the second position representing a stomach of the subject and having a second depth relative to the anterior surface of the subject, wherein confirmation of an insertion path of the catheter, in three-dimensions, is enabled based on the graphical representation of an insertion path of the catheter including:
  (i) the graphical representation of the first portion of the catheter at the first position of the reference image, and
  (ii) the graphical representation of the second portion of the catheter at the second position of the reference image.

* * * * *